United States Patent
Wheatley et al.

(10) Patent No.: US 11,686,891 B2
(45) Date of Patent: *Jun. 27, 2023

(54) ANGULARLY AND SPECTRALLY SELECTIVE DETECTOR AND LIGHT SOURCE SYSTEMS

(71) Applicant: 3M INNOVATIVE PROPERTIES COMPANY, St. Paul, MN (US)

(72) Inventors: John A. Wheatley, Stillwater, MN (US); Gilles J. Benoit, Minneapolis, MN (US); Guanglei Du, Painted Post, NY (US); Steven R. Anderson, Woodbury, MN (US); Owen M. Anderson, Minneapolis, MN (US); David T. Yust, Woodbury, MN (US); Rolf W. Biernath, Wyoming, MN (US); Gary E. Gaides, Woodbury, MN (US); Brian W. Lueck, Houlton, WI (US); Neeraj Sharma, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 428 days.

This patent is subject to a terminal disclaimer.

(21) Appl. No.: 16/462,249

(22) PCT Filed: Dec. 1, 2016

(86) PCT No.: PCT/US2016/064302
§ 371 (c)(1),
(2) Date: May 20, 2019

(87) PCT Pub. No.: WO2018/097841
PCT Pub. Date: May 31, 2018

(65) Prior Publication Data
US 2019/0339431 A1    Nov. 7, 2019

Related U.S. Application Data

(60) Provisional application No. 62/425,353, filed on Nov. 22, 2016.

(51) Int. Cl.
*G02B 5/08* (2006.01)
*G02B 5/22* (2006.01)
(Continued)

(52) U.S. Cl.
CPC .............. *G02B 5/22* (2013.01); *G01J 3/0229* (2013.01); *A61B 5/02427* (2013.01); *A61B 5/681* (2013.01); *G02B 2207/123* (2013.01)

(58) Field of Classification Search
CPC . G02B 5/00; G02B 5/003; G02B 5/20; G02B 5/201; G02B 5/208; G02B 5/22; G02B 2207/123; G02B 5/12
(Continued)

(56) References Cited

U.S. PATENT DOCUMENTS 6,398,370 B1    6/2002 Chiu
6,939,015 B2 *  9/2005 Hodge ............... H01L 31/02164
                                           257/E31.122

(Continued)

FOREIGN PATENT DOCUMENTS

JP    S63-275920      11/1988
JP    2014150143       8/2014
(Continued)

OTHER PUBLICATIONS

International Search Report for PCT International Application No. PCT/US2016/064302, dated Nov. 22, 2017, 7 pages.

*Primary Examiner* — Thong Q Nguyen
(74) *Attorney, Agent, or Firm* — Robert S. Moshrefzadeh

(57) ABSTRACT

A detector system is described that includes a detector that is sensitive to wavelengths in a detection wavelength range. The detector system further includes a light control film that is disposed on the detector and includes a plurality of alternating first and second regions. Each first region has a width W and a height H, where H/W≥1. Each first region has
(Continued)

a substantially low transmission in a first portion of the detection wavelength range and a substantially high transmission in the remaining portion of the detection wavelength range. Each second region has a substantially high transmission in the detection wavelength range.

10 Claims, 12 Drawing Sheets

(51) Int. Cl.
  *G01J 3/02* (2006.01)
  *A61B 5/024* (2006.01)
  *A61B 5/00* (2006.01)
(58) Field of Classification Search
  USPC ............... 359/599–614, 515–553, 599–613
  See application file for complete search history.

(56) References Cited

U.S. PATENT DOCUMENTS

| | | | |
|---|---|---|---|
| 8,213,082 B2 | 7/2012 | Gaides | |
| 8,659,829 B2 | 2/2014 | Walker, Jr. | |
| 8,891,169 B2 | 11/2014 | Kashiwagi | |
| 9,229,253 B2 | 1/2016 | Schwartz | |
| 9,229,261 B2 | 1/2016 | Schwartz | |
| 2005/0213245 A1* | 9/2005 | Katsura | G02B 5/021 359/443 |
| 2005/0243428 A1* | 11/2005 | Takahashi | G02B 6/0051 359/599 |
| 2010/0283947 A1 | 11/2010 | Nishihara et al. | |
| 2011/0116025 A1 | 5/2011 | Park et al. | |
| 2011/0205632 A1 | 8/2011 | Park | |
| 2013/0050798 A1 | 2/2013 | Kim | |
| 2014/0175404 A1 | 6/2014 | Shim | |
| 2014/0204464 A1 | 7/2014 | Halverson | |
| 2014/0346469 A1 | 11/2014 | Shin | |
| 2014/0353626 A1 | 12/2014 | Shim | |
| 2014/0353645 A1 | 12/2014 | Jeong | |
| 2015/0009563 A1 | 1/2015 | Lauters | |
| 2015/0102327 A1 | 4/2015 | Kim | |
| 2015/0102328 A1 | 4/2015 | Shin | |
| 2016/0254312 A1* | 9/2016 | Lee | G02B 27/30 382/125 |

FOREIGN PATENT DOCUMENTS

| | | |
|---|---|---|
| WO | WO 00/46890 | 8/2000 |
| WO | WO 2009-108190 | 9/2009 |
| WO | WO 2014-103342 | 7/2014 |
| WO | WO 2018-097842 | 5/2018 |

* cited by examiner

ANGULARLY AND SPECTRALLY SELECTIVE DETECTOR AND LIGHT SOURCE SYSTEMS

FIELD OF INVENTION

The present invention relates generally to light control films, and more specifically to spectrally selective and angular selective light control films for use in various optical applications such as optical communication systems having a light source, an optical construction, and/or detector system.

BACKGROUND

The louver structure is known in the art of privacy films in display devices or window applications applied to, for example, building, houses, etc. In the case of privacy films, when a user does not want others to see the contents of a screen of an electronic display device, the user can physically apply a privacy film to the screen such that images can be viewed selectively. Typically, images being displayed on the screen can be viewed through the privacy film only when the viewer is positioned within a range of angles referred to as "viewing angle". Normally, the viewing angle is some range of angles centered on an axis normal to the surface of the privacy film. As the position of the viewer changes such that the viewer is positioned outside the viewing angle, images being displayed are less or no longer viewable.

In the case of window applications, the louver structure is typically a window blind or shutter with horizontal slats that are angled to admit background light but keep out direct sunshine. The amount of light that can go through the louver structure depends on the angle of the slats (or the louver orientation).

SUMMARY

Generally, the present invention relates to light control films. The present invention also relates to light control films that have different viewing angle for different wavelength ranges.

In one embodiment of the invention a light control film includes a plurality of spaced apart first regions, where each first region has a substantially low transmission in one or two of a first wavelength range from about 300 nm to about 400 nm, a second wavelength range from about 400 nm to about 700 nm, and a third wavelength range from about 700 nm to about 1200 nm, and a substantially high transmission in the remaining wavelength ranges. The light control film has a first viewing angle of less than about 70 degrees along a predetermined first direction. In some cases, the light control film has a second viewing angle of less than about 70 degrees along an orthogonal predetermined second direction different from the first viewing angle. In some cases, the light control film of claim 1 includes a major microstructured first surface having a plurality of alternating ribs and channels, where each channel is at least partially filled with a first material to form one of the first regions in the plurality of spaced apart first regions. In some case, the light control film also includes a plurality of second regions that alternate with the plurality of first regions. In such cases, each second region may have a substantially high transmission in each wavelength range the first regions have a substantially low transmission in.

In another embodiment, a light control film includes a major microstructured first surface having a plurality of alternating ribs and channels. Each channel is at least partially filled with a first material. Each channel has a width W and a height H, where $H/W \geq 1$. Each rib includes a second material, where the absorption of at least one of the first and second materials varies as a function of wavelength in a range from about 300 nm to about 1200. In some cases, the absorption of each of the first and second materials varies as a function of wavelength in a range from about 400 nm to about 1200.

In another embodiment, a light control film includes a plurality of spaced apart first regions and a second region. Each first region has a substantially low transmission in a first wavelength range from about 700 nm to about 1200 nm, and the second region has a substantially low transmission in a second wavelength range from about 300 nm to about 400 nm.

In another embodiment, a light control film includes a plurality of spaced apart first regions and a second region. Each first region has a substantially low transmission in at least one of a first wavelength range from about 300 nm to about 400 nm, a second wavelength range from about 400 nm to about 700 nm, and a third wavelength range from about 700 nm to about 1200 nm. The second region has a substantially low transmission in at least one of the at least one of the three wavelength ranges each first region has substantially low transmission in. In some cases, each first region and the second region have substantially low transmission in the same two of the three wavelength ranges.

In another embodiment, a light control film includes a plurality of spaced apart first regions and a second region. Each first region has a substantially high transmission in a first wavelength range from about 300 nm to about 400 nm and a substantially low transmission in a second wavelength range from about 400 nm to about 700 nm. The second region has a substantially high transmission in each of the first and second wavelength regions.

In some embodiments, a detector system includes a detector that is sensitive to wavelengths in a detection wavelength range. The detector system further includes a light control film that is disposed on the detector and includes a plurality of alternating first and second regions, where each first region has a width W and a height H, $H/W \geq 1$. Each first region has a substantially low transmission in a first portion of the detection wavelength range and a substantially high transmission in the remaining portions of the detection wavelength range. Each second region has a substantially high transmission in the detection wavelength range. In some cases, the detection wavelength range is from about 800 to about 1600 and the first portion of the detection wavelength range is from about 900 nm to about 1100 nm.

In some embodiments, a light control film includes a plurality of spaced apart first regions and a second region, where each first region has a width W and a height H, $H/W \geq 1$. Each first region has substantially low transmissions in each of non-overlapping predetermined first and second wavelength ranges. The second region has a substantially low transmission in the predetermined second wavelength range. In some cases, the predetermined first wavelength range includes shorter wavelengths and the predetermined second wavelength range includes longer wavelengths.

In some embodiments, a light control film includes a plurality of spaced apart first regions and a second region. Each first region has a width W and a height H, $H/W \geq 1$, and a substantially low transmissions in each of non-overlapping predetermined first and second wavelength ranges. The second region has substantially high transmission in the predetermined second wavelength range.

In some embodiments, a light control film includes a plurality of spaced apart first regions and a second region. Each first region has a width W and a height H, H/W≥1, and a substantially high transmission in a predetermined first wavelength range and a substantially low transmission in a predetermined non-overlapping second wavelength range. The second region has substantially high transmission in each of the predetermined first and second wavelength ranges.

In some embodiments, a light control film includes a plurality of spaced apart first regions and a second region, where each first region has a width W and a height H, H/W≥1, and a substantially low transmission in a predetermined first wavelength range and a substantially high transmission in a predetermined non-overlapping second wavelength range. Each second region has substantially low transmission in each of the predetermined first and second wavelength ranges.

In some embodiments, a light control film includes a plurality of spaced apart first regions and a second region. Each first region has a width W and a height H, H/W≥1, and a substantially high transmission in a predetermined first wavelength range and a substantially low transmission in a predetermined non-overlapping second wavelength range. The second region has substantially low transmission in each of the predetermined first and second wavelength ranges.

In some embodiments, a light control film includes a plurality of spaced apart first regions and a second region, where each first region has a width W and a height H, H/W≥1, and a substantially low transmission in a predetermined first wavelength range and a substantially high transmission in a predetermined non-overlapping second wavelength range. The second region has substantially high transmission in each of the predetermined first and second wavelength ranges.

In some embodiments, a light control film is configured to block light in a predetermined wavelength range and includes a plurality of spaced apart first regions. Each first region has a width W and a height H, H/W≥1, and a substantially high transmission in a predetermined first wavelength range, a substantially low transmission in a predetermined second wavelength range, and a substantially high transmission in a predetermined third wavelength range. The second wavelength range is disposed between the first and third wavelength ranges In some embodiments, a light control film includes a plurality of spaced apart first regions and a second region, such that for light incident normally to a plane of the light control film an average optical transmittance of the light control film is less than about 10% in a predetermined first wavelength range having shorter wavelengths, and an average optical transmittance of the light control film is greater than about 50% in a predetermined second wavelength range having longer wavelengths. Furthermore, for light incident at or greater than about 30 degrees from the plane of the light control film an average optical transmittance of the light control film is less than about 20% in each of the predetermined first and second wavelength ranges.

In some embodiments, a light control film includes a plurality of spaced apart first regions and a second region, such that when an angle of incidence of light incident on the light control film changes from about 90 degrees to about 60 degrees relative to a plane of the light control film, an average optical transmittance of the light control film changes by less than about 10% in a predetermined first wavelength range having shorter wavelengths, and greater than about 40% in a predetermined second wavelength range having longer wavelengths.

In some embodiments, a light control film includes a major microstructured first surface that includes a plurality of alternating ribs and channels. Each channel is at least partially filled with a first material to form a first region. The light control further includes a second region positioned adjacent at least a portion of at least one first region. The second region includes a second material. Each of the first and second materials absorbs light in one or two of a first wavelength range from about 300 nm to about 400 nm, a second wavelength range from about 400 nm to about 700 nm, and a third wavelength range from about 700 nm to about 1200 nm. Each channel includes a width W and a height H, where H/W≥1.

In some embodiments, a light source system includes a light source that is configured to emit light having a first spectral profile along a first direction and a second spectral profile along a different second direction. The light source system further includes a light control film that is disposed on the light source for receiving and transmitting light emitted by the light source. The light control film includes a plurality of spaced apart first regions. Each first region has a width W and a height H, where H/W≥1. The first regions are oriented relative to the first and second directions and have a spectral absorbance profile so that when light emitted by the light source is transmitted by the light control film, the transmitted light has a third spectral profile along the first direction and a fourth spectral profile along the second direction, where the difference between the third and fourth spectral profiles is less than the difference between the first and second spectral profiles.

In some embodiments, a retroreflective system includes a retroreflective sheet for retroreflecting light, and a light control film that is disposed on the retroreflective sheet. For a first wavelength, light incident on the light control film at each of a first and second angles of incidence is retroreflected, and for a second wavelength, light incident on the light control film at the first, but not the second, angle of incidence is retroreflected. In some cases, the light control film has a greater first viewing angle for the first wavelength and a smaller viewing angle for the second wavelength.

BRIEF DESCRIPTION OF THE DRAWINGS

The invention may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

DETAILED DESCRIPTION

Figure 1:
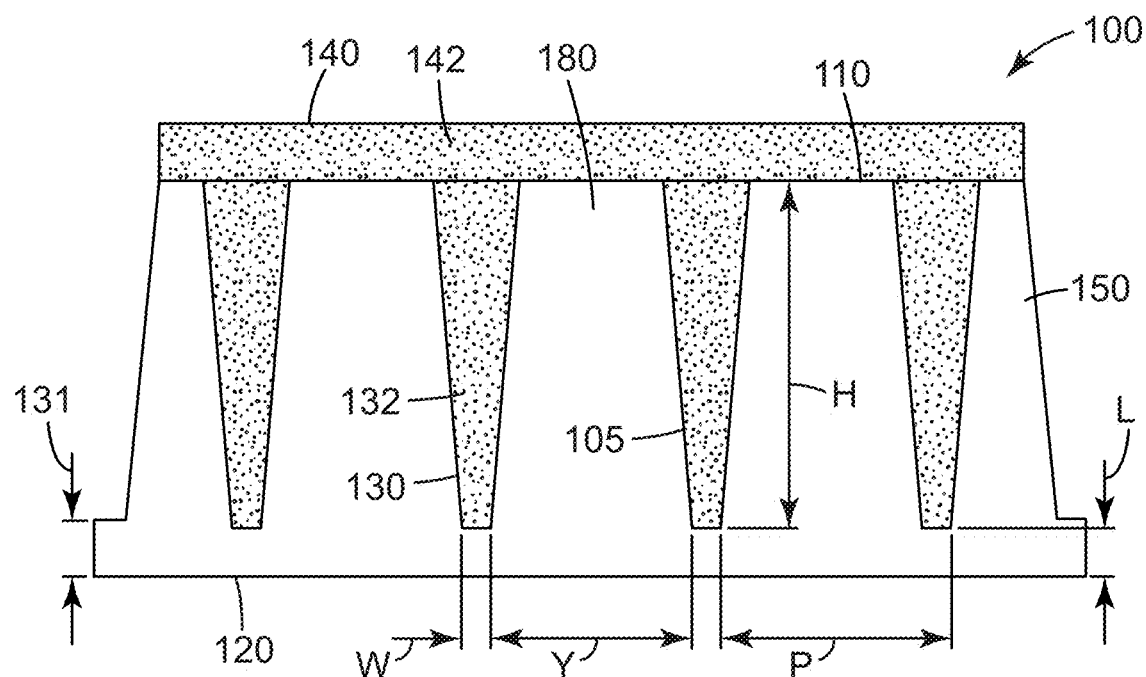
FIGS. 1, 1A, 1B, 1C, 1D, 1E, 1F and 1G are schematic cross-sectional views of exemplary light control films.
Figure 1A:
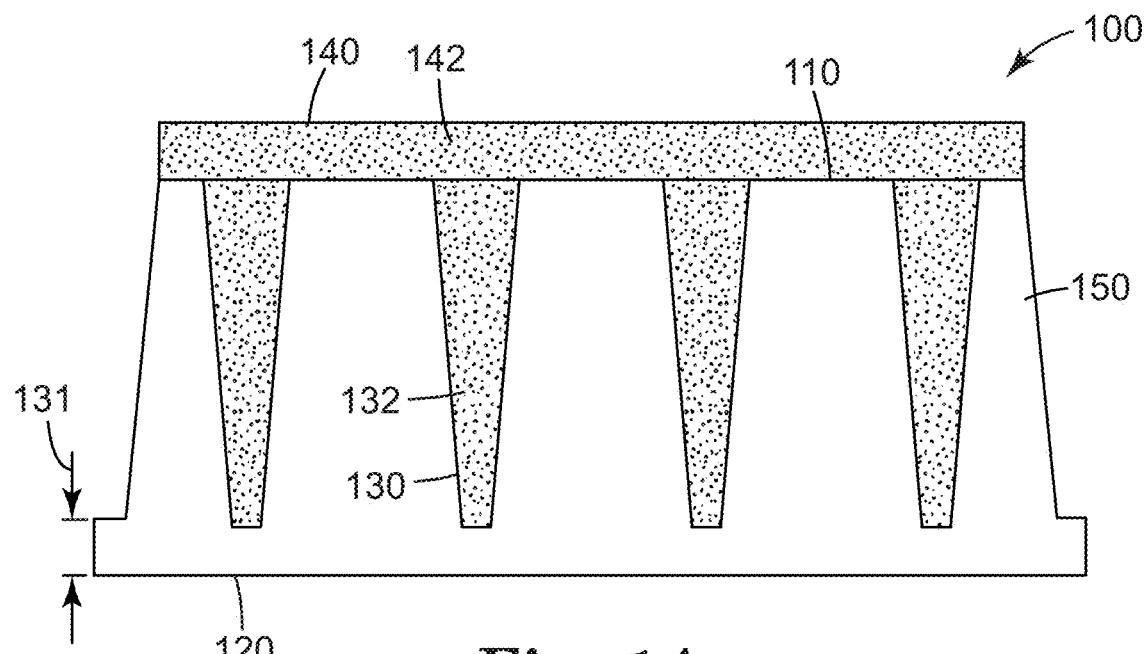

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

The louver structure is known as having angle selectivity such that in privacy applications, such as when the louver structure is placed in front of a display, a viewer can see the displayed images only when the viewer is within the viewing angle of the louver structure, and in window applications, such as when the louver structure is placed on, for example, a building window, the sun light can go through the window only for light rays that are within the viewing angle of the louver structure. The "viewing angle" is defined herein with respect to the normal to the plane of the structure as the range of angles over which the louver structure is substantially transmissive. For example, the viewing angle of a light control film may be defined as the range of angles over which the transmission of the light control film is within 60%, or within 50%, or within 40% of the peak transmission. One type of the louver structure in the privacy film which typically includes a substantially transparent louver film disposed on a polymeric substrate where the louvers include light absorbing material resulting in alternating transparent and light absorbing regions. The light absorbing regions are relatively positioned to provide a restricted viewing angle. Exemplary louver structures are described in U.S. Pat. No. 6,398,370 B1 (Chiu et al.), U.S. Pat. No. 8,213,082 B2 (Gaides et al.) and U.S. Pat. No. 9,229,253 B2 (Schwartz et al.).

The louver structures disclosed herein may be applied to various optical applications such as optical communication systems having a light source, an optical construction, and/or a detector system where the optical construction includes a light control film to make the optical communication systems angle selective and/or spectral selective. In some cases, in addition to one or more louver structures, an optical communication system may also have other films or structures to provide additional or enhanced angle selectivity. The louver structures, and other films or structures may have 2 dimensional or 3 dimensional structures. Exemplary additional structures that may be included in an optical communication system include optical diffusers, brightness enhancement films and reflective polarizers. In some embodiments, the disclosed light control films include light absorbing or reflecting regions including light absorbing or reflecting materials that make the regions wavelength selective (spectral selective). In some embodiments, the light control film has at least two different types of materials and each material may absorb or reflect light differently in at least a part of at least one of ultraviolet, visible and infrared wavelength ranges. With the variety of combinations among the louver structures and the light absorbing or reflecting materials, the light control film can have a variety of angle selectivity and wavelength selectivity (spectral selectivity) so that the light control film can be applied in many applications for variety of purposes.

Figure 1B:
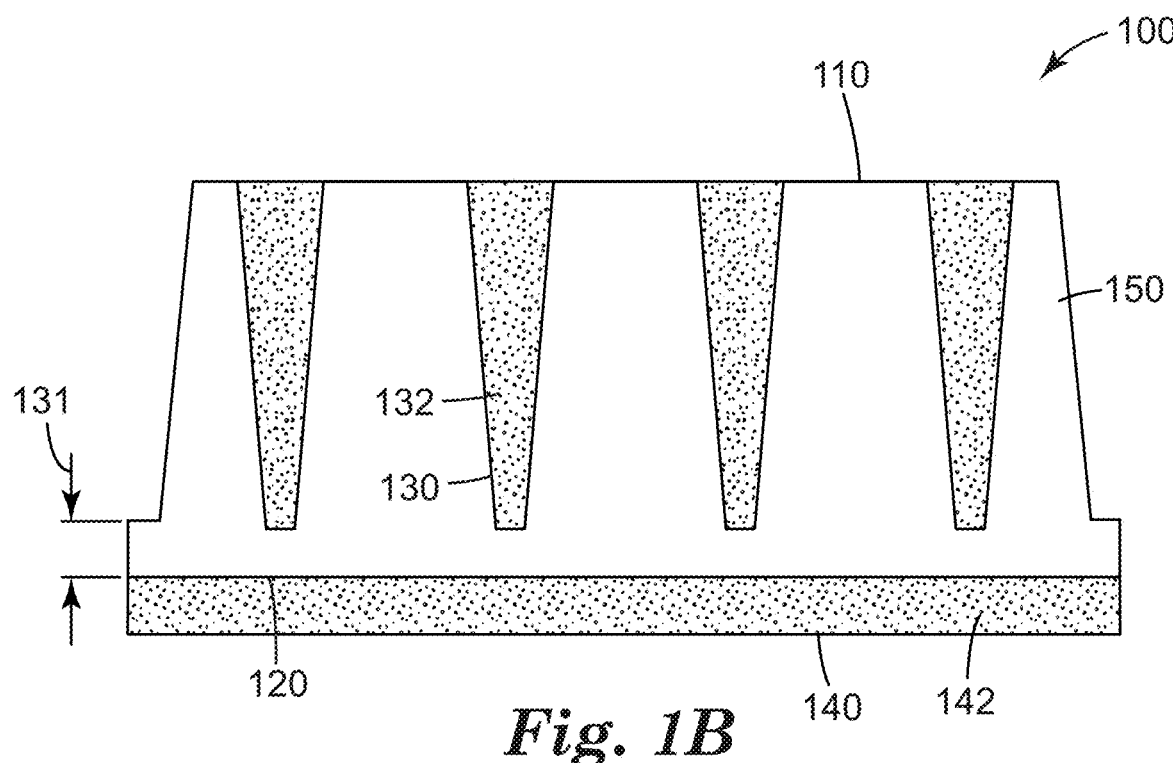
Figure 1C:
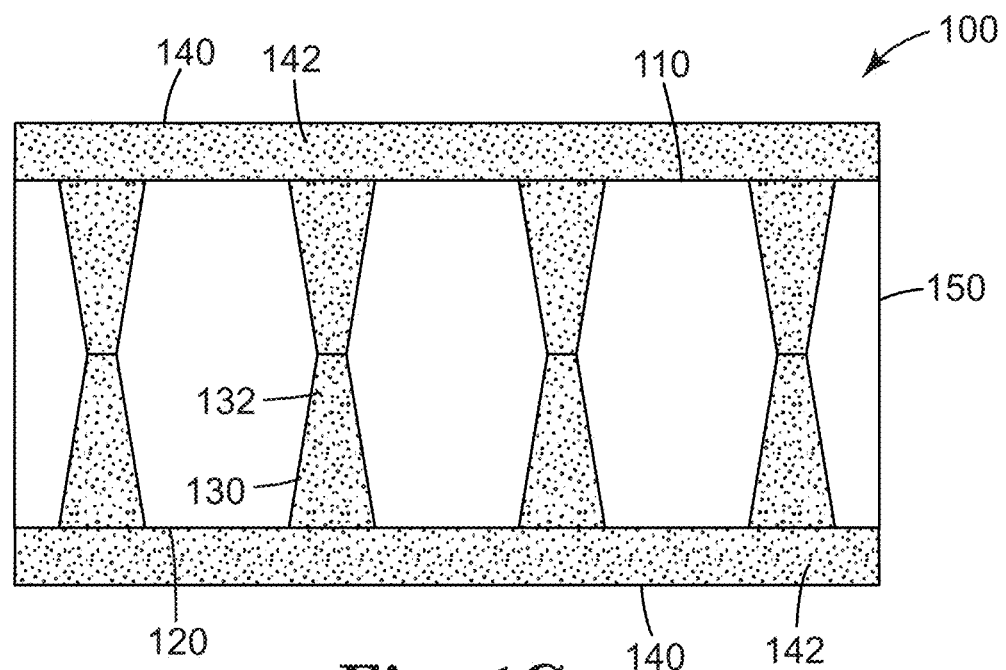
Figure 1D:
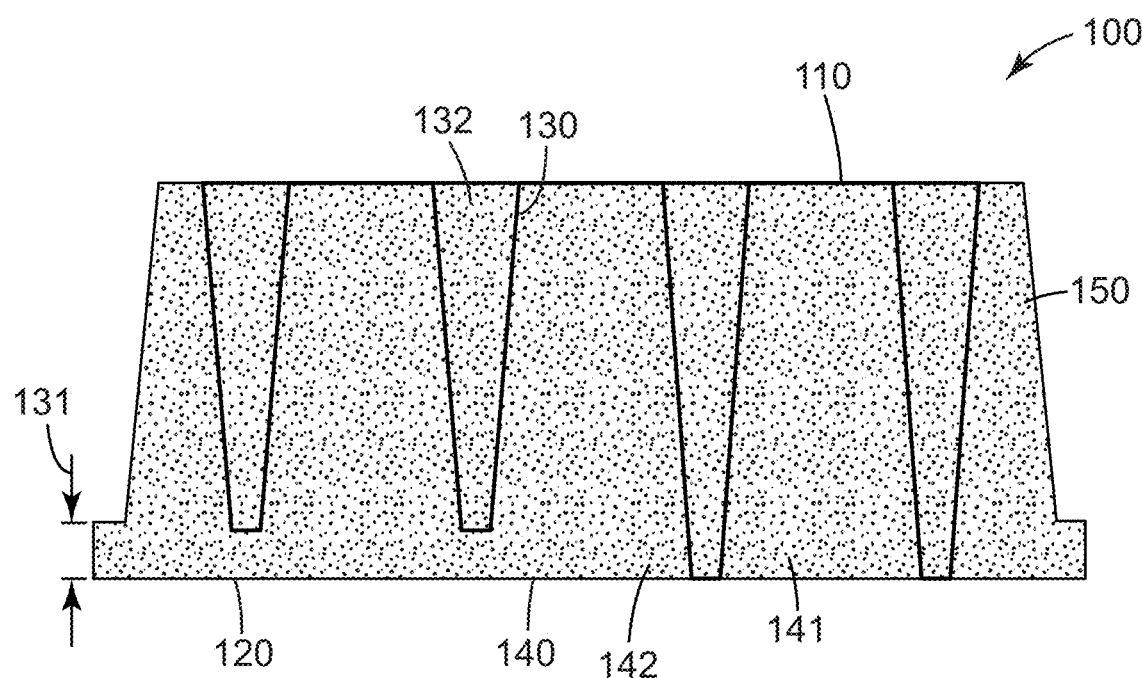
Figure 1E:
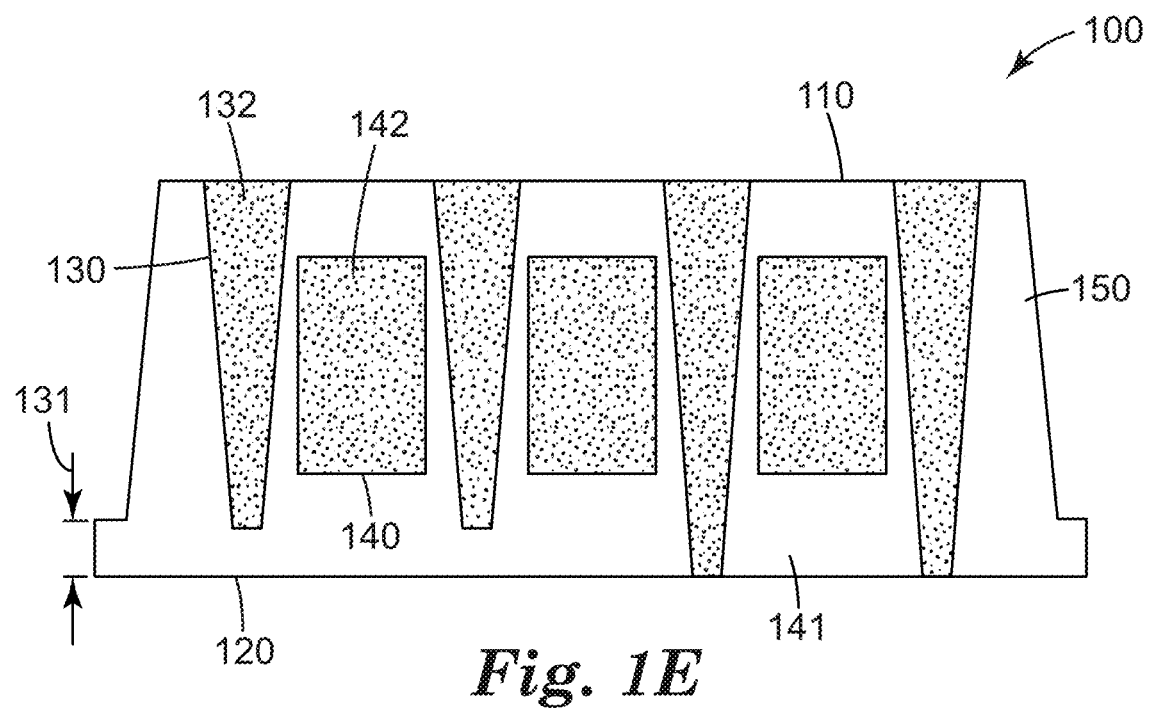
Figure 1F:
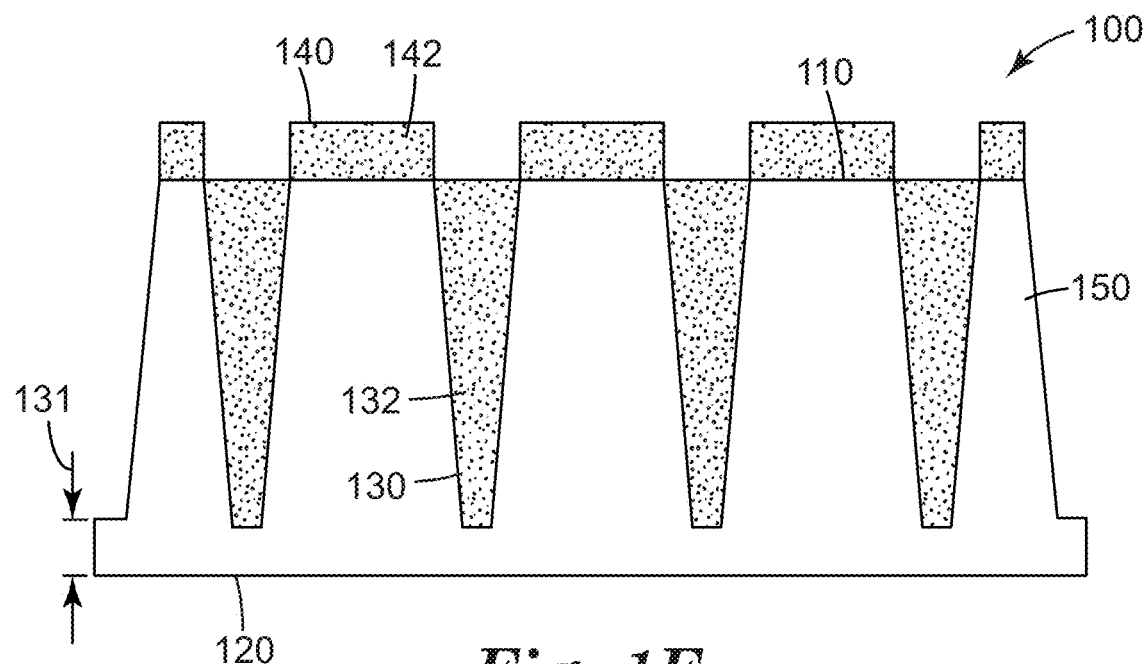
Figure 1G:
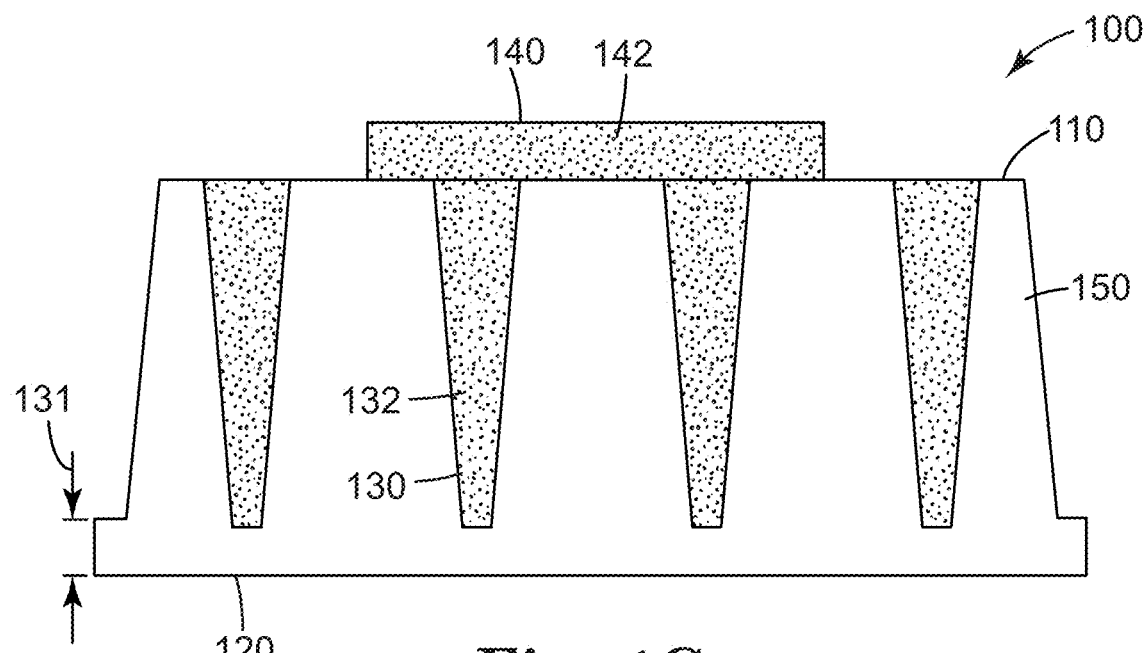

FIG. 1 and FIGS. 1A-1G show schematic cross-sectional views of exemplary optical films that may be useful in forming a light control film (LCF). A LCF 100 includes an optical film 150 and the optical film 150 has a major first surface 110 and a major second surface 120 opposed to the first surface 110. The optical film 150 includes at least one microstructured surface. For example, either the first surface 110 or the second surface 120 or both surfaces may be microstructured. For instance, FIGS. 1A, 1D, 1F and 1G, show that the first surface 110 is microstructured and FIG. 1B shows that the second surface 120 is microstructured and FIG. 1C shows that both major surfaces 110 and 120 are microstructured. While the major surfaces 110 and 120 are referred to as the respective first surface and the second surface for reference purposes, it will be recognized that in use, the first surface may be facing a viewer or a light source, the second surface may be facing a viewer or a light source, or either the first surface or the second surface may be facing both a viewer and a light source. Microstructures are generally projections, protrusions and/or indentations in the surface of an article that deviate in profile from an average center line drawn through the microstructure. For example, as shown in FIG. 1, the first surface 110 has a plurality of alternating ribs 180 and channels 130 extending across the first surface 110 of the optical film 150. Each channel 130 is at least partially filled with a first material 132 to form a first region. In some cases, such as in the case of the LCF 100 shown schematically in, for example, FIGS. 1A and 1B, channels 130 do not extend across the entire thickness of the optical film 150 resulting in a continuous land 131 between the base of the channels 130 and the second surface 120 of the optical film 150. In some cases, such as in the case of the LCF 100 shown schematically in FIG. 1D, at least some of the channels 130 extend all the way through the thickness of the optical film 150 resulting in no or a discontinuous land 131. In some cases, the channels 130 may become first regions by at least partially filling each channel with a first material 132. As shown in FIG. 1C, the channels or the first regions 130 may be formed on both the first surface 110 and the second surface 120 of the optical film 150. In some cases, the optical film 150 also includes a second region 140 that is adjacent at least a portion of at least one first region and includes a second material 142. In the exemplary embodiments shown in FIGS. 1A, 1B, 1C, 1F and 1G, the second region 140 is formed on at least one of the first surface 110 and second surface 120. The second region 140 in these embodiments may be coated, printed or laminated with the second material 142 on at least one of the first surface 110 and second surface 120. As another example, in FIG. 1D, the second region 140 is formed inside the optical film 150 between and/or below the first regions 130. In general, in the case of alternating first and second regions, the second regions may have a connecting portion, for example, in the form of a land portion, connecting the second regions near at least one of the first and second major surfaces, where the connecting or land portion may or may not be continuous. For example, the second regions 140 are connected by a discontinuous land 131. As another example, in FIG. 1E, the second regions 140 are connected to one another near each of the major surfaces by continuous land portions 131. Furthermore, in some cases, such as the exemplary light control film 100 shown in FIG. 1E, the second region 140 include a plurality of second region segments alternating with the plurality of first regions 130. In some cases, the second region 140 is formed on at least portion or portions of the first surface 110 and/or second surface 120. For example, the second region 140 is formed on a portion or spaced part portions of the first surface 110, as shown in FIGS. 1F and 1G, where in the exemplary embodiment shown in FIG. 1G, the second region 140 is disposed on at least portions of the ribs 180. As shown in FIG. 1F, the second region 140 is formed on spaced apart portions of the first surface 110 resulting in a discontinuous second region having a plurality of second region segments 140 alternating with the first regions 130. In each of the exemplary embodiments shown in FIGS. 1D and 1G, the first and second regions alternate, and each second region has a width W and a height W. In FIG. 1D, H/W is typically greater than 1 or greater than 2 or greater than 5, and in FIG. 1G, W/H is typically greater than 1 or greater than 2 or greater than 5. Furthermore, as shown in FIG. 1G, the second region 140 is disposed on at least portions of the ribs 180. In general, the first regions 130 and the second region 140 may be formed in the same layer or different layers of the LCF 100. For example, in FIGS. 1A, 1B, 1F and 1G, the first and second regions 130 and 140 are formed in two neighboring layers of the LCF 100. As another example, in FIGS. 1D and 1E, the first and second regions 130 and 140 are both formed in the same optical film 150. Moreover, each of the first and second materials 132 and 142 absorbs and/or reflects light in one or two of a first ultraviolet wavelength range from about 300 nm to about 400 nm, a second visible wavelength range from about 400 nm to about 700 nm, and a third near infrared wavelength range from about 700 nm to about 1200 nm. In some cases, such as in the exemplary embodiment shown in FIG. 1, each channel 130 and each rib 180 has a height H. Furthermore, each channel 130 has a width W and each rib 180 has a width Y, and pitch P indicates spacing of the channels 130 and the ribs 180. Width Y of the rib is P-W. The land 131 has a height L such that the thickness of the film 150 is H+L. The channel aspect ratio for the film 150 is defined as H/W, and rib aspect ratio as H/Y. In some cases, H/W≥1, or H/W≥2, or H/W≥5, or H/W≥10, or H/W≥20. In some embodiments, the rib aspect ratio H/Y is greater than about 0.1, or 0.5, or 1 or 1.5, or greater than about 2.0, or greater than about 3.0. In some cases, the height of the land 131 (L) is typically minimized to optimize light absorption once the channels 130 are filled with the first material 132 such as light absorbers or reflectors while sufficiently thick to support a large number of ribs 180. The exemplary ribs 180 in FIG. 1 have sides or walls 105 that are substantially parallel to each other, although, in general, the walls 105 may be angled and have any shape that may be desirable in an application such as shown, for example, in FIG. 4 of U.S. Pat. No. 9,229,261 (Schwartz et al.). Parameters "H", "W", "P", "Y", "L" and indices of refraction of the LCF materials may have any suitable values as long as the LCF 100 functions as desired.

Figure 2:
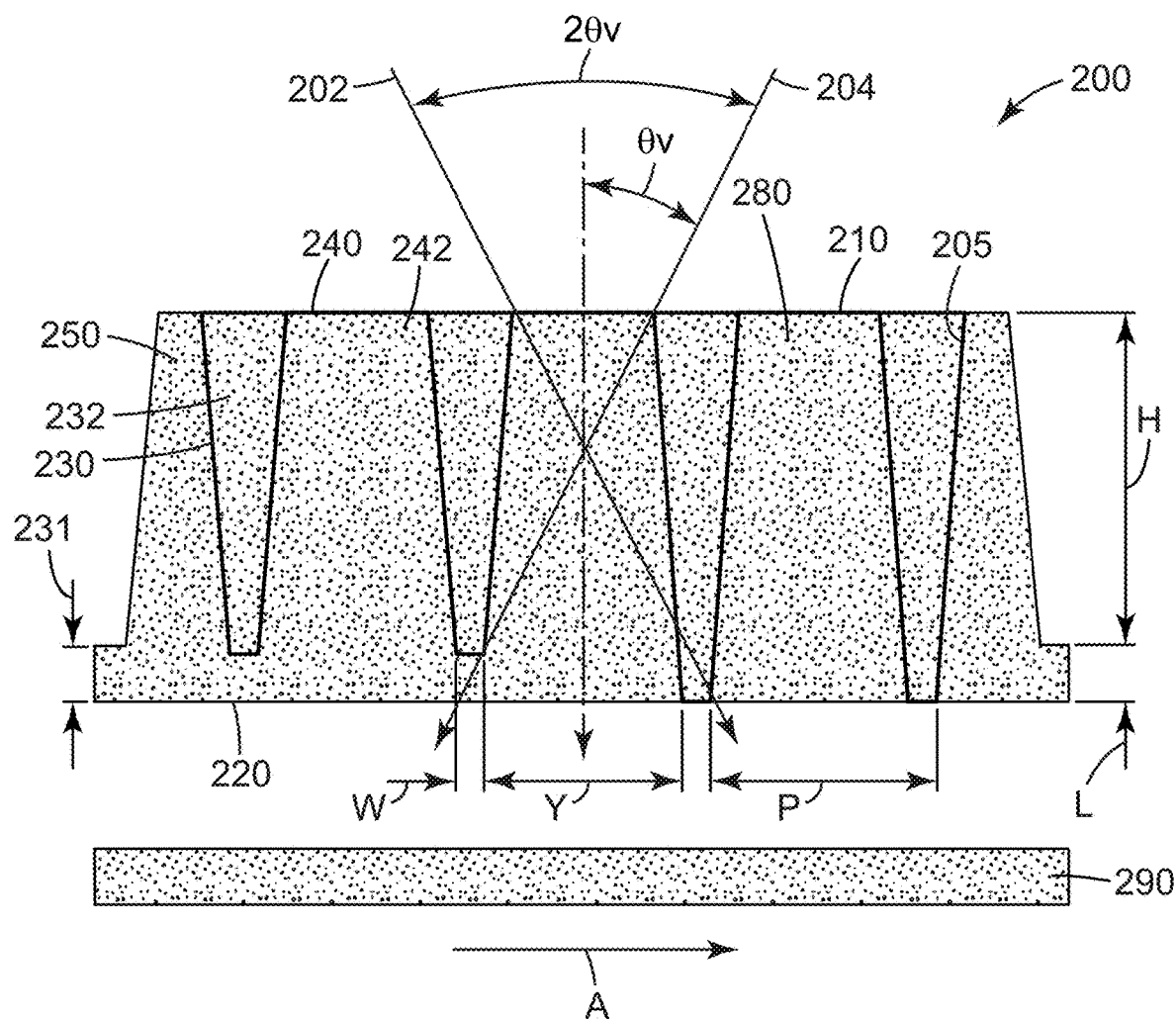
FIG. 2 is a schematic cross-sectional view of an exemplary optical communication system.

FIG. 2 shows partial schematic cross-sectional view of another exemplary optical film that may be useful in forming a light control film (LCF). LCF 200 includes an optical film 250 and the optical film 250 has a major microstructured first surface 210 and a major second surface 220 opposed to the first surface 210. The microstructured first surface 210 has a plurality of alternating ribs 280 and channels 230 extending across the first surface 210 of the optical film 250. Each channel 230 is at least partially filled with a first material 232 to form at least one of first regions 230 in the plurality of spaced apart first regions 230. At least one of the ribs 280 a second material 242 to form a second region 240. A continuous land 231 may be present between the base of the channels 230 and the second surface 220. Each channels 230 and ribs 280 has a height H. Each channels 230 has a width W and each ribs 280 has a width Y, and pitch P indicates spacing of the channels 230 and the ribs 280. Width Y of the rib is P-W. The land 231 has a height L such that the thickness of the film 250 is H+L. The spacing and shape of the channels 230 and/or the ribs 280 determine viewing angle 2θv, where 2θv is the angle between limiting light rays 202 and 204 transmitted by channels 230 without reflection from walls 205. In general, parameters/dimensions of the channels/ribs are selected such that a desired viewing angle 2θv is provided by the LCF 200. In one aspect, the viewing angle 2θv ranges from 10 degree to 80 degree or, or about 10 degrees to about 70 degrees. In some cases, the viewing angle is less than about 80 degrees, or less than about 75 degrees, or less than about 70 degrees, or less than about 65 degrees, or less than about 60 degrees, or less than about 55 degrees, or less than about 50 degrees, or less than about 45 degrees, or less than about 40 degrees, or less than about 35 degrees, or less than about 30 degrees, or less than about 25 degrees, or less than about 20 degrees, or less than about 15 degrees, or less than about 10 degrees, or less than about 5 degrees. In general, it is desirable for the LCF parameters to be selected such that an adequate amount of light can pass through the optical film 250. In some cases, narrower channels width W and larger pitch P may lead to increased viewing angle 2θv and the amount of light passing through the LCF 200 may be increased. In some cases, increasing the channel aspect ratio (H/W) and reducing the pitch "P" may decrease the viewing angle 2θv. In some cases, a LCF 200 includes a plurality of spaced apart first regions 230. Each first region 230 has a substantially low transmission in one or two of a first wavelength range from about 300 nm to about 400 nm, a second wavelength range from about 400 nm to about 700 nm, and a third wavelength range from about 700 nm to about 1200 nm, and a substantially high transmission in remaining wavelength ranges. In some embodiments, the LCF 200 includes a first viewing angle 2θv of less than about 70 degrees along a predetermined first direction A.

Figure 2A:
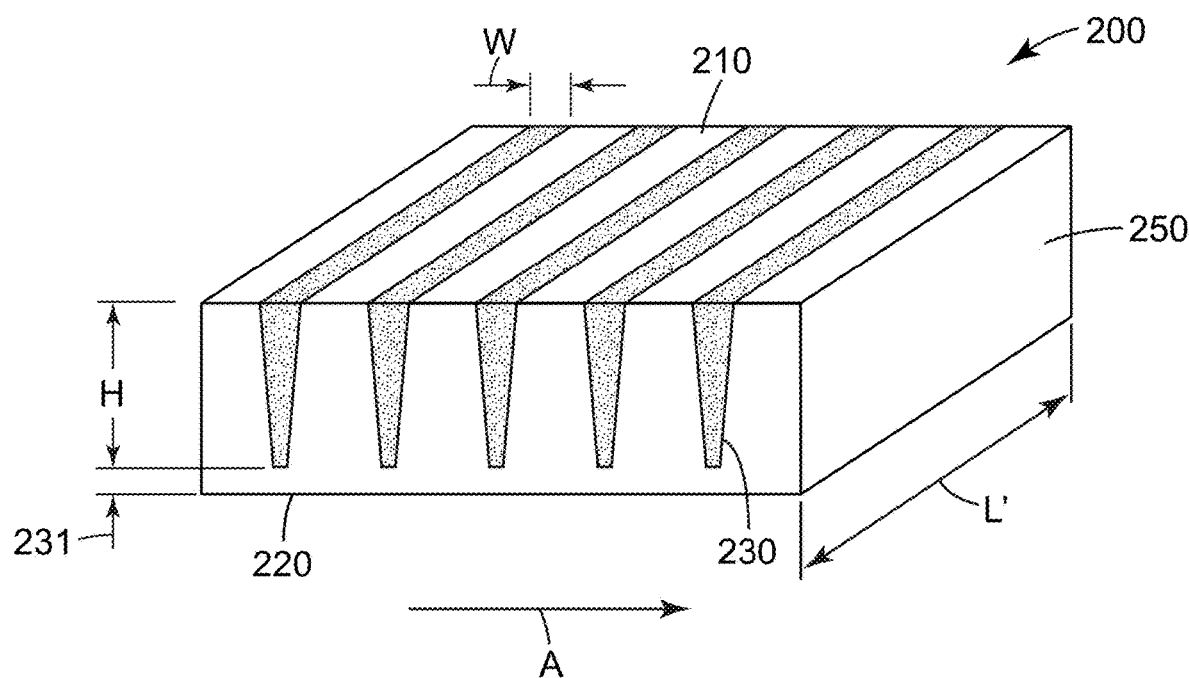
FIGS. 2A and 2B are schematic perspective views of exemplary light control films.
Figure 2B:
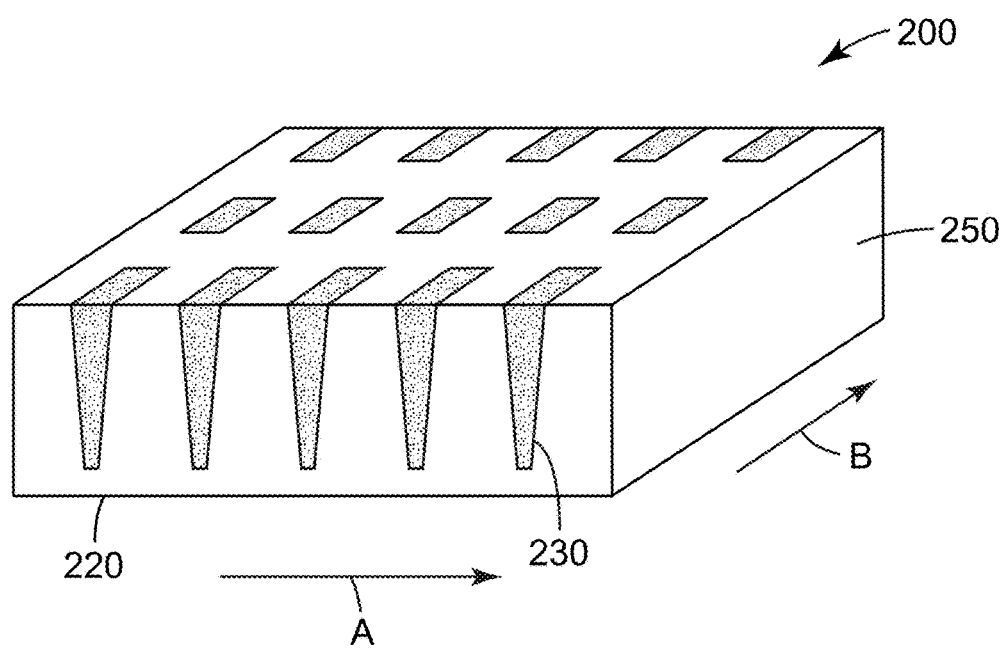

In some embodiments, LCF 200 includes a plurality of spaced apart parallel first regions 230. LCF 200 also includes an optical film 250 having a major first surface 210 and an opposing major second surface 220. The plurality of first regions 230 are formed in the major first surface 210 and extend into the optical film 250 and may or may not reach the major surface second 220. In the exemplary LCF 200 shown in FIG. 2A, the first regions 230 may be generally referred to as two-dimensional regions or structures meaning that the width W and the height H of each region 230 are much smaller than the length L' of the first region 230. As such, each first region 230 may be thought of as having finite extents along two dimensions (width W and height H) while extending infinitely along the third dimension (length L'). As shown in FIG. 2A, the first regions 230 are extended along a first direction "A" and the LCF 200 has a first viewing angle 2θv along the first direction "A". In some cases, the first viewing angle 2θv along the predetermined first direction A may be less than about 70 degrees, or less than about 60 degrees, or less than about 50 degrees, or less than about 40 degrees, or less than about 30 degrees. In some embodiments, LCF 200 may have three-dimensional first regions 230 having finite extents along three mutually orthogonal directions. For example, FIG. 2B shows another LCF 200 that includes a plurality of three-dimensional first regions 230 extending into the optical film 250 from the first surface 210 toward the second surface 220. As shown in FIG. 2B, the first regions 230 are extended along a first direction "A" and also extended along a second direction "B". The LCF 200 has a first viewing angle 2θv along the first direction "A" and a second viewing angle along an orthogonal predetermined second direction "B", where the second viewing angle may be equal to or different from the first viewing angle 2θv. In some cases, the first viewing angle 2θv along the predetermined first direction "A" may be less than about 70 degrees, or less than about 60 degrees, or less than about 50 degrees, or less than about 40 degrees, or less than about 30 degrees. In some embodiments, the second viewing angle along the predetermined second direction "B" may be less than about 70 degrees, or less than about 60 degrees, or less than about 50 degrees, or less than about 40 degrees, or less than about 30 degrees. The cross-sectional views of the first regions 230 perpendicular to the thickness direction may be square, rectangle, triangle, circle, ellipse, or any combination thereof, or any shape that may be desirable in an application. In general, an LCF may include one or more of the optical films disclosed herein combined with other films such as those described in, for example, U.S. Pat. No. 6,398,370 incorporated herein in its entirety. In some cases, the first regions 230 in FIG. 2B may be posts, pyramids, cones, truncated cones, truncated pyramids, hemispheres, or any shape that may be desirable in an application. Furthermore, the first regions 230 may be asymmetric structures, symmetric structures, tilted structures, spatially variant structures, and any other structure that may be desirable in an application such as any structure that includes angular-dependent light transmitting or light blocking capabilities. In some embodiments, each rib 280 has a substantially high transmission in each wavelength range that the first regions 230 have a substantially low transmission in. In other embodiments, each rib 280 has a substantially low transmission in at least one wavelength range that the first regions 230 have a substantially high transmission in. In some cases, the LCF 200 includes a plurality of second regions 240 alternating with the plurality of first regions 230, each second region 240 having a substantially high transmission in each wavelength range the first regions 230 have a substantially low transmission in. In some embodiments, the LCF 200 includes a plurality of second regions 240 alternating with the plurality of first regions 230, each second region 240 having a substantially low transmission in at least one wavelength range the first regions 230 have a substantially high transmission in. In some examples, the LCF 200 may includes a second region 240 extending across and covering at least some of the first regions 230 as shown in FIGS. 1A, 1B, 1F and 1G. The second region 240 has a substantially low transmission in at most one, but not all, wavelength regions the first regions 230 have a substantially high transmission in. In some embodiments, the first wavelength range is from about 350 nm to about 400 nm, or from about 350 nm to about 380 nm. In some embodiments, the second wavelength range is from about 400 nm to about 460 nm, or from about 470 nm to about 550 nm. In some embodiments, the third wavelength range is from about 800 nm to about 1000 nm, or from about 820 nm to about 1200 nm, or from about 885 nm to about 1200 nm, or from about 920 nm to about 1200 nm.

In some cases, an LCF 200, for example as shown in FIG. 2, may includes a major microstructured first surface 210 having a plurality of alternating ribs 280 and channels 230. Each channel 230 is at least partially filled with a first material 232. The channel aspect ratio for the optical film 250 is defined as H/W. In some cases, the aspect ratio H/W is at least 1 (H/W≥1), or H/W≥2, or H/W≥5, or H/W≥10, or H/W≥20. Each rib 280 includes a second material 242. In some cases, an absorption of at least one of the first and second materials 232 and 242 varies as a function of wavelength in a range from about 400 nm to about 1200. In other cases, the absorption of each of the first and second materials 232 and 242 varies as a function of wavelength in a range from about 400 nm to about 1200.

Figure 3:
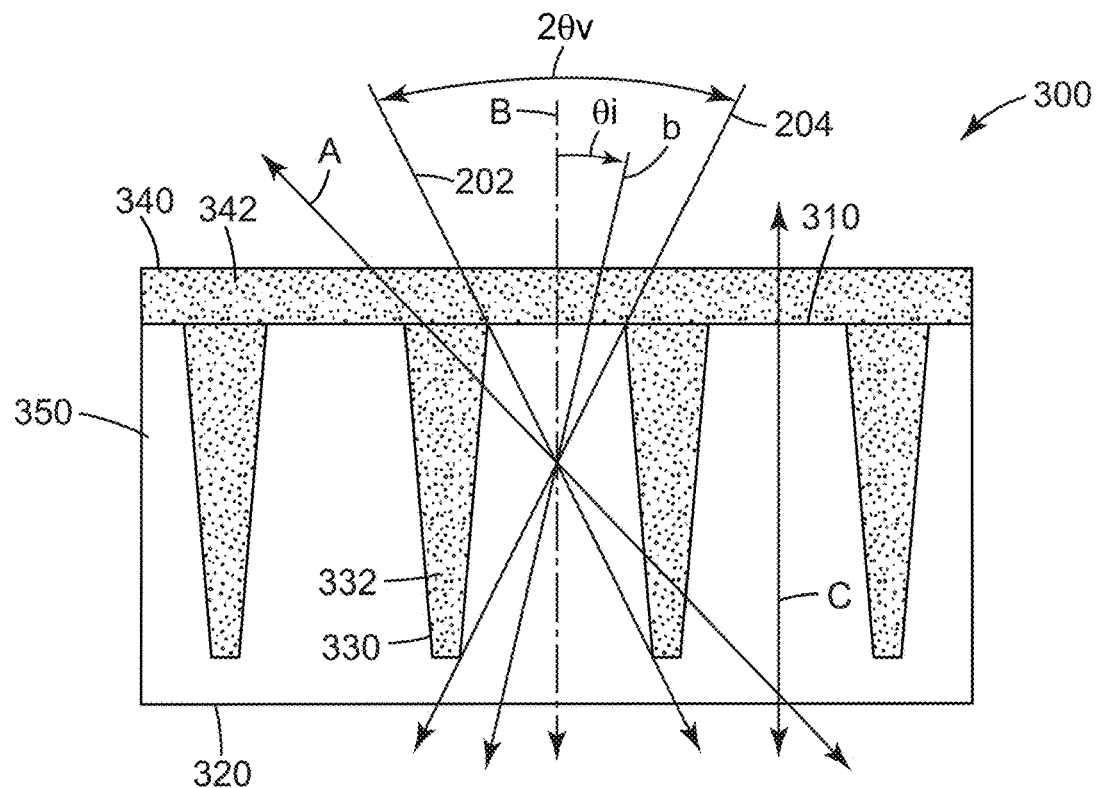
FIG. 3 is a schematic cross-sectional view of an exemplary light control film.

FIG. 3 shows a schematic cross-sectional view of an exemplary optical film that may be useful in forming a light control film (LCF). As shown in FIG. 3, an optical film 350 includes a major first surface 310 and a plurality of spaced apart substantially parallel first regions 330 formed in, and extending from, the major first surface toward an opposing major second surface 320, and a second region 340 provided on the major first surface 310 and extending across and covering the plurality of first regions 330. The first regions 330 may be filled at least partially with a first material 332 and the second region 340 may include a second material 342. In some cases, the first material 332 and the second material 342 absorb, reflect or block light to have a substantially low transmission in one or two of a first wavelength range from about 300 nm to about 400 nm, a second wavelength range from about 400 nm to about 700 nm, and a third wavelength range from about 700 nm to about 1200 nm, and a substantially high transmission in the remaining wavelength ranges. In some cases, the second region 340 may be coated, printed or laminated with the second material 342 on at least one of the first surface 310 and second surface 320. In some embodiments, the first material 332 or the second material 342 may include a pigment, a dye, a black colorant such as a carbon black, or combinations thereof so that the first and second materials 332 and 342 may absorb or reflect light. A variety of light absorbers or light reflectors may be used in the disclosed LCFs. For example, several compositions of visibly transparent infrared absorbing transparent conducting oxides (TCOs) both as thin films and nanoparticle powders and dispersions may be included useful in the disclosed LCFs. Exemplary TCOs include indium tin oxide (ITO), antimony tin oxide (ATO), gallium tin oxide (GTO), antimony zinc oxide (AZO), aluminum/indium doped zinc oxide, doped tungsten oxides like cesium tungsten oxides, and tungsten blue oxides. Other visibly transparent infrared absorbers include metal borides like lanthanum hexaborides, and conducting polymer nanoparticles like PEDOT-PSS. Metal chalcogenides like metal sulfides and selenides also absorb infrared light including, for example, copper sulfide and copper selenide nanoparticles, tungsten disulfides and molybdenum disulfides. Another class of visibly transparent tunable infrared absorbers are metallic plasmonic nanoparticles such as those made of gold, silver copper etc. Moreover, near infrared dyes and pigments may be applied to the disclosed LCFs. These dyes have low visible absorption but strong narrow band infrared absorption. Many of these dyes and pigments are organic/ organometallic or metal organic in nature. Some of major classes of dyes/pigments include phthalocyanines, cyanine, transitional metal dithioline, squarilium, croconium, quniones, anthraquinones, iminium, pyriliu, thiapyrilium, azulenium, azo, perylene and indoanilines. Many of these dyes and pigments can exhibit both visible and/or infrared lights absorption as well. Further, many different types of visible dyes and colorants may be used with the disclosed LCFs and they fall in one or more classes like acid dyes, azoic coloring matters, coupling components, diazo components. Basic dyes include developers, direct dyes, disperse dyes, fluorescent brightners, food dyes, ingrain dyes, leather dyes, mordant dyes, natural dyes and pigments, oxidation bases, pigments, reactive dyes, reducing agents, solvent dyes, sulfur dyes, condense sulfur dyes, vat dyes. Some of the organic pigments may belong to one of more monoazo, azo condensation insoluble metal salts of acid dyes and disazo, naphthols, arylides, diarylides, pyrazolone, acetoarylides, naphthanilides, phthalocyanines, anthraquinone, perylene, flavanthrone, triphendioxazine, metal complexes, quinacridone, polypryrrolopyrrole etc. Moreover, metal oxide pigments may be used in the disclosed LCFs. For example, metal chromates, molybdates, titanates, tungstates, aluminates, ferrites are some of the common pigments. Many contain transition metals like iron, managanese, nickel, titanium, vanadium, antimony, cobalt, lead, cadmium, chromium etc. Bismuth vanadates are non-cadmium yellows. These pigments may be milled to create nanoparticles which may be useful where transparency and low scattering is desired. In some examples, the first or second materials 332 or 342 may be a particulate materials having an average particle size less than 10 microns, or 1 micron, or less. The first or second materials 332 or 342 may, in some embodiments, have a mean particle size of less than 1 micron. In some embodiments, the first or second materials 332 or 342 may be dispersed in a suitable binder. In some embodiments, rather than in the form of particles, the first or second materials 332 or 342 may be a light absorbing resin, such as a light absorbing polymer, at least partially forming light absorbing regions 330 and 340. In some cases, the first regions 330 may include particles or scattering elements that may function to block light from being transmitted through the first regions 330. In some cases, at least one of the first material 332 and the second material 342 may be selected among the materials that are spectrally selective in at least a part of at least one of ultraviolet, visible and infrared light ranges. In some cases, both the first material 332 and the second material 342 may be selected among the materials that are spectrally selective in at least a part of at least one of ultraviolet, visible and infrared light ranges so that a transmission of a light passing through the LCF 300 is spectrally selective in at least two of the ultraviolet, visible and infrared light ranges. Stated differently, the first and second materials 332 and 342 are spectrally selective in at least a part of ultraviolet, visible and infrared light ranges in order to make the transmission vary as a function of wavelength of light. As shown in FIG. 3, a "light B" propagates along an axis that is normal to the plane of the LCF 300. As described herein, by "normal" to the LCF is meant perpendicular to the plane of the LCF, discounting any local variation in the smoothness of the LCF where the variation may, for example, be general surface roughness or a regular microstructure formed in a major surface of the LCF. For the purpose of this disclosure, the angle between an incident light ray "b" and the normal to the LCF is referred to as the "incidence angle, θi". For example, the incidence angle of light B is zero. In general, the incidence angle may range from 0 degree (i.e. normal to the film) to 90 degree (i.e. parallel to the film). Therefore, "normal incidence angle" may mean incident perpendicularly to the film, discounting any local variation in the LCF. In some embodiments, at the normal incidence angle where a viewer is looking at an image through the LCF 300 in a direction that is perpendicular to the film surface, the image is viewable and brightest and the transmission of a light passing through the LCF 300 may be greatest. In some embodiments, such as when the channels or first regions 330 are symmetric and oriented perpendicularly to the LCF 300, as the incidence angle increases, the amount of light transmitted through the LCF 300 decreases until the incidence angle reaches the viewing angle 2θv from which point on substantially all the light is blocked by the first material 332 as shown in FIG. 3 as a "light A" and the image is no longer viewable. In some embodiments, the transmission of a light passing through the second region 340 and at least partially absorbed by the second material 342 is substantially uniform for at least one incidence angle. For example, the transmission of a "light C" as shown in the FIG. 3, passing through the second region 340 and being partially absorbed by the second material 342 and exiting the LCF 300 (without going through the first regions 330 or being absorbed by the first material 332) is substantially uniform. In some embodiments, second region 340 absorbs some light in a pre-determined wavelength range, and in some cases, absorbs substantially all incident light having wavelengths in the pre-determined wavelength range. In some cases, the optical transmission of a light C having a wavelength in the pre-determined wavelength range and passing through the second region 340 may be less than about 10%, where in some cases, the transmission may be substantially independent from the incidence angle of the light C. In some cases, in order to achieve the transmission of a light having a wavelength in the pre-determined wavelength range and passing through the second region 340 be less than about 10%, thickness or size of the second materials 342 may be increased, or the second region 340 might include multiple layers of the second materials 342, or the multiple layers of the second materials 342 may be provided on at least one of the first surface 310 and second surface 320, or either first or second surfaces 310 and 320 may include multiple layers of the second materials 342, or the concentration of the second materials 342 may be increased. In some cases, the transmission of a light having a wavelength in the pre-determined wavelength range may be less than 10% by providing scattering particles in and/or on the optical film 350.

In some embodiments, the optical film 350 described in the present invention may also include a base substrate layer (not shown), which may be integrally formed with, or separately added to the optical film 350 (whether by extrusion, cast-and-cure, or any other known that may be suitable in a desired application). The chemical composition and thickness of the base material may depend on the requirements of the product that is being constructed. That is, balancing the needs for strength, clarity, optical retardance, temperature resistance, surface energy, adherence to the other layers, among others, as specifically described in, for example, U.S. Pat. No. 8,213,082 (Gaides et al.) incorporated herein in its entirety. In some embodiments, the optical film 350 may be combined with a cover layer that may provide, for instance, an anti-glare coating, an anti-reflective coating, an anti-soiling coating, or some combination thereof. Materials for the base substrate layer or the cover layer may include, for instance, polycarbonate. The particular polycarbonate material may be selected so as to provide a matte finish or a glossy finish. The cover layer and base substrate layer may be each or both be matte or/and glossy. The cover layer may be bonded to the second region 340 or the major first surface 310 of the optical film 350 with an adhesive. The adhesive may be any optically clear adhesive, such as a UV-curable acrylate adhesive, a transfer adhesive, and the like. Moreover, the LCF 300 may include any number of other films or layers including, for example, polarizing film, wavelength selective interference filter layer, prismatic film to form multilayer structures.

In some embodiments, the disclosed light control or optical films, such as optical film 350, may be prepared by molding and ultraviolet curing a polymerizable resin on a polycarbonate substrate. Such processing are currently used to make known optical films available from 3M Company, St. Paul, Minn., under the trade designation. An exemplary manufacturing method and suitable composition for known optical films are described in U.S. Pat. No. 8,213,082 (Gaides et al.).

Figure 4:
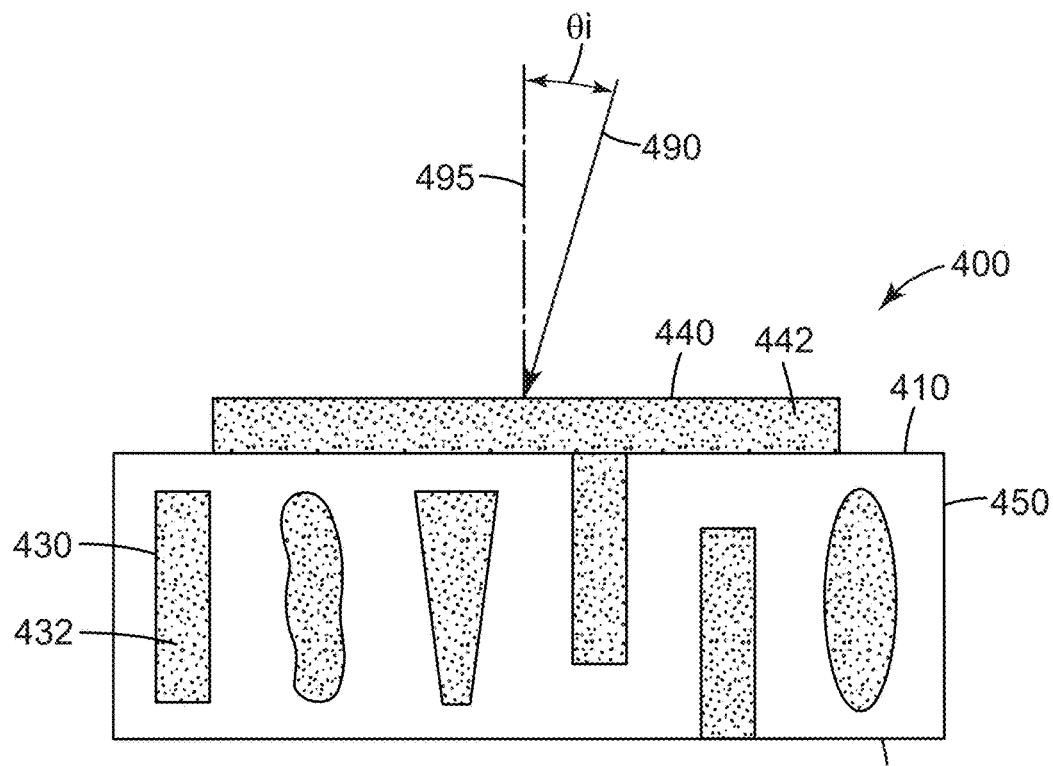
FIG. 4 is a schematic cross-sectional view of another exemplary light control film.

Referring to FIG. 4, a light control film (LCF) 400 includes a plurality of spaced apart first regions 430. Each first region 430 includes a first material 432. As shown in FIG. 4, the first regions 430 may have a wide variety of shapes and may extend from either/both the first surface 410 or/and the second surface 420 or be formed in the middle of the optical film 450. The first material 432 substantially absorbs or/and reflects light in a first wavelength range and substantially transmits light in a different second wavelength range. For example, in some cases, the first material 432 absorbs or/and reflects at least 70%, or at least 80%, or at least 90%, or at least 95% of light in the first wavelength range, and transmits at least 70%, or at least 80%, or at least 90%, or at least 95% of light in the second wavelength range. In some cases, the first wavelength range is an infrared light range, and the second wavelength range is a visible light range. For example, in some cases, the first wavelength range may be from about 700 nm to about 1200 nm, and the second wavelength range may be from about 400 nm to about 700 nm. LCF 400 further includes a second region 440 disposed adjacent at least a portion of at least one first region 430. In some cases, such as in the exemplary embodiment of the LCF 400 shown in FIG. 4, second region 440 extends across a majority, but not all, of the first regions 430. In some cases, second region 440 may extend across all first regions 430. The second region 440 includes a second material 442 that substantially absorbs or/and reflects light in a third wavelength range and substantially transmits light in a fourth wavelength range different from the third wavelength range. For example, in some cases, the second material 442 absorbs or/and reflects at least 70%, or at least 80%, or at least 90%, or at least 95% of light in the third wavelength range, and transmits at least 70%, or at least 80%, or at least 90%, or at least 95% of light in the fourth wavelength range. In some cases, the third wavelength range is a ultraviolet light range, and the fourth wavelength range is a visible light range. For example, in some cases, the third wavelength range may be from about 350 nm to about 400 nm, and the fourth wavelength range may be from about 400 nm to about 700 nm. The transmission of a light 490 passing through the LCF 400 varies as a function of an incidence angle ($\theta i$) (the angle between an incident light 490 and the normal 495 to the LCF) and a wavelength of the light. For example, the transmission is: (1) no more than about 10% of incident light in a ultraviolet light range substantially independent of the incidence angle; (2) greater than about 40% for light in a visible light range substantially independent of the incidence angle; (3) greater than about 40% for light in an infrared light range for the incidence angles within a viewing angle ($2\theta v$ refer to the FIG. 2); and (4) less than about 10% for light in the infrared light range for the incidence angles outside the viewing angle.

In some embodiments, as shown in FIG. 1, an LCF 100 includes a plurality of spaced apart first regions 130 and a second region 140. Each first region 130 may have a substantially low transmission in a first near infrared wavelength range from about 700 nm to about 1200 nm and the second region 140 may have a substantially low transmission in a second ultraviolet wavelength range from about 300 nm to about 400 nm. The second region 140 is adjacent at least a portion of at least one first region 130. In the exemplary embodiments shown in FIGS. 1A, 1B 1F and 1G, the second region 140 is formed on at least one of the respective first surface 110 and second surface 120. As another example, in FIG. 1D, the second region 140 is formed in the optical film 150 between and/or below the first regions 130. In some embodiments, when at least some of the first regions 130 may extend all the way through the thickness of the optical film 150, the second region 140 is formed between channels 130 resulting in a plurality of spaced apart second regions 141 interconnected via a land 131 which in some cases, may be continuous and in some other cases, may be discontinuous. Further, in some cases, as shown in FIG. 1E, the second region 140 includes a plurality of segments alternating with the plurality of first regions 130. In some cases, the second region 140 is disposed in at least portions of the ribs 180. In some embodiments, the second region 140 is formed on at least one of the first surface 110. As shown in FIGS. 1F and 1G, the second region 140 is partially formed on the first surface 110 and/or second surface 120. As shown in FIG. 1F, the second region 140 may be partially formed on the first surface 110 alternating with the first regions 130. Furthermore, as shown in FIG. 1G, the second region 140 is disposed on at least portions of the ribs 180.

In some embodiments, as shown in FIG. 1, an LCF 100 includes a plurality of spaced apart first regions 130 and a second region 140. Each first region 130 may have a substantially low transmission in at least one of a first wavelength range from about 300 nm to about 400 nm and a second wavelength range from about 400 nm to about 700 nm, and a third wavelength range from about 700 to about 1200 nm. The second region 140 may have a substantially low transmission in at least one of the at least one of the three wavelength ranges each first region has substantially low transmission in. In some cases, each first region 130 and the second region 140 may have substantially low transmission in the same two of the three wavelength ranges. LCF 100 includes a major microstructured first surface 110 that includes a plurality of alternating ribs 180 and channels 130, where each channel is at least partially filled with a first material 132 to form one of the first regions 130 in the plurality of spaced apart first regions. In some cases, the second region 140 includes a plurality of second region segments, and each rib includes one of the second region segments. In some cases, the second region 140 is disposed on the major surface 110 of the light control film, where, in some cases, the second region extends across and covers at least some of the first regions 130.

In some embodiments, as shown in FIG. 1, a LCF 100 includes a plurality of spaced apart first regions 130 and a second region 140. Each first region 130 may have a substantially high transmission in a first wavelength range from about 300 nm to about 400 nm and a substantially low transmission in a second wavelength range from about 400 nm to about 700 nm. The second regions 140 may have a substantially high transmission in each of the first and second wavelength regions. In some cases, each first region 130 and the second region 140 may have substantially high transmissions in a third wavelength range from about 700 nm to about 1200 nm. In some examples, each first region 130 may have a substantially low transmission region in a third wavelength range from about 700 nm to about 1200 nm, and the second region has a substantially high transmission region in the third wavelength range.

Figure 5:
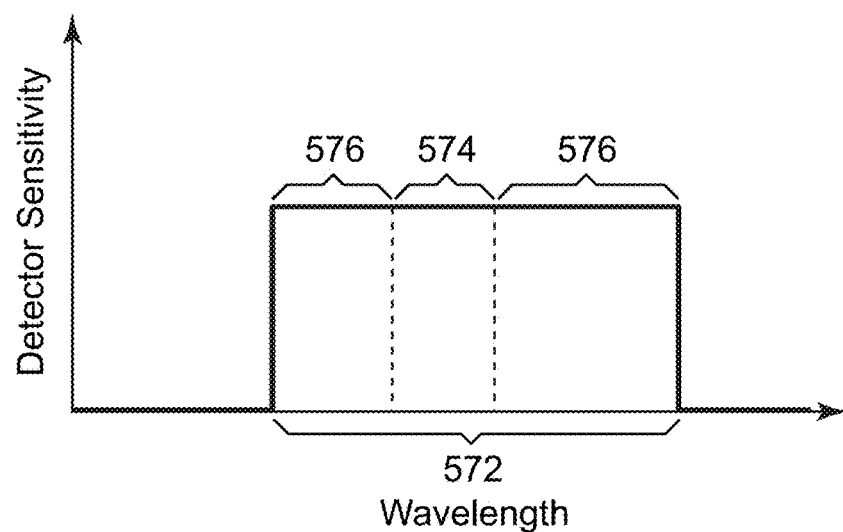
FIG. 5 is a schematic plot of detector sensitivity vs. wavelength.

In some examples, the light control films (LCFs) disclosed herein may be part of an optical communication system. The "optical communication system" as referred to herein is a system that is for communication of light over a distance from a light source through a disclosed LCF to a target, where the target may include a detector or human eye and the light source my include ambient light. In general the light source the light source may be any light source desirable in an application. Exemplary light source include a light emitting diode (LED), a laser light source, a halogen light source, a metal halide light source, a tungsten light source, a mercury vapor light source, a short arc xenon light source, or the sun. In some cases, the LCFs disclosed herein may be part of an optical communication system with a detector system. In some cases, the detector system may provide various types of outputs, such as electronic signals, when receiving light passing through the LCF of the optical communication system. In an exemplary examples as shown in FIG. 2, a detector system includes a detector 290 that is sensitive to wavelengths in a detection wavelength range and an LCF 200 disposed on the detector 290. The LCF 200 includes a plurality of alternating first and second regions 230 and 240. Each first region 230 has a width W and a height H and an aspect ratio H/W. In some cases, the aspect ratio H/W is at least 1 (H/W≥1), or H/W≥2, or H/W≥5, or H/W≥10, or H/W≥20. FIG. 5 schematically shows the relation between the detector sensitivity and wavelength illustrating that the detector is sensitive to wavelengths in the detection wavelength range 572. Each first region 230 has a substantially low transmission in a first portion 574 of the detection wavelength range 572 and a substantially high transmission in the remaining portion 576 of the detection wavelength range. Each second region has a substantially high transmission in the detection wavelength range 572. In some cases, the detection wavelength range 572 is from about 800 nm to about 1600 nm and the first portion 574 of the detection wavelength range 572 is from about 900 nm to about 1100 nm. In some examples, a viewing angle 2θv of the LCF in the first portion 574 of the detection wavelength range 572 is less than about 70 degrees along a first direction "A" (referring to FIG. 2, 2A or 2B). In some cases, the detector is or includes a photovoltaic device. In some cases, the detector is configured to detect solar radiation, for example, to charge a battery. In such cases, the detector is or may include a solar battery, a solar cell, or a solar detector. In some cases, the detector may be the detector in a camera for detecting and/or recording an image. In some cases, the detector may be a in a camera or camera system. In some cases, a camera may include the detector system of FIG. 2.

In some cases, as shown in FIG. 2, an LCF 200 includes a plurality of spaced apart first regions 230 and a second region 240. Each first region 230 has a width W and a height H and an aspect ratio H/W that is at least 1 (H/W≥1) or H/W≥2, or H/W≥5, or H/W≥10, or H/W≥20. Each first region 230 has substantially low transmissions in each of non-overlapping predetermined first and second wavelength ranges and the second region 240 has a substantially low transmission in the predetermined second wavelength range. Specifically, the predetermined first wavelength range may include shorter wavelengths and the predetermined second wavelength range may include longer wavelengths. In some cases, the predetermined first wavelength range may be from about 400 nm to about 700 nm and the predetermined second wavelength range may be from about 700 nm to about 1200 nm. In some cases, the average optical transmittance of each first region 230 in the predetermined first wavelength range may be less than about 25, or 15%, or 10%, or 5%, or 1%, or 0.1%, or 0.01%, or 0.001, or 0.0001%. In some cases, the average optical transmittance of each first region 230 in the predetermined second wavelength range is less than about 25, or 15%, or 10%%, or 5%, or 1%, or 0.1%, or 0.01%, or 0.001, or 0.0001. In some cases, the average optical transmittance of the second region 240 in the predetermined second wavelength range may be less than about 25, or 15%, or 10%%, or 5%, or 1%, or 0.1%, or 0.01%, or 0.001, or 0.0001. Each first region 230 may have a substantially high absorption in the predetermined first wavelength range. For example, the average optical absorption of each first region 230 in the predetermined second wavelength range may be greater than about 70%, or 80%, or 90%, or 95%, or 99%. Each first region may have a substantially high reflectance in the predetermined first wavelength range. For example, the average optical reflectance of each first region 230 in the predetermined second wavelength range may be greater than about 70%, or 80%, or 90%, or 95%, or 99%. In general, each first region 230 may have a first index of refraction, and the second region may have a second index of refraction. In some embodiments, it may be desirable to substantially match indices of refraction between the first regions and the regions between them and/or between the first regions and the second region. In some cases, a difference between the first and second indices of refraction may be less than about 0.01. In some cases, the second region 240 may have a substantially low transmission in the predetermined first wavelength range. In such cases, the average optical transmittance of the second region 240 in the predetermined second wavelength range may be less than about 10%. In some embodiments, the second region 240 may have a substantially high transmission in the predetermined first wavelength range. In such cases, the average optical transmittance of the second region 240 in the predetermined first wavelength range may be greater than about 70%. The second region 140 may include a plurality of segments alternating with the plurality of first regions 130 as shown in, for example, FIG. 1E. In some cases, the second region 140 may extend across and cover at least some of the first regions 130 as shown in, for example, FIGS. 1, 1A, 1B, 1F and 1G. Furthermore, in some cases, the second region 140 may be discontinuous as shown in, for example, FIGS. 1E and 1F.

In some embodiments, as shown in FIG. 2, an LCF 200 includes a plurality of spaced apart first regions 230 and a second region 240. Each first region 230 may have a width W and a height H and an aspect ratio H/W that is at least 1 (H/W≥1) or H/W≥2, or H/W≥5, or H/W≥10, or H/W≥20. Each first region may have substantially low transmissions in each of non-overlapping predetermined first and second wavelength ranges and the second region 240 may have substantially high transmission in the predetermined second wavelength range. In exemplary embodiments, the predetermined first wavelength range may include shorter wavelengths and the predetermined second wavelength range may include longer wavelengths. In some cases, the predetermined first wavelength range may be from about 400 nm to about 700 nm and the predetermined second wavelength range may be from about 700 nm to about 1200 nm. In some cases, the average optical transmittance of each first region 230 in the predetermined first wavelength range may be less than about 10%. In some cases, the average optical transmittance of each first region in the predetermined second wavelength range may be less than about 10%. In some cases, the average optical transmittance of the second region in the predetermined second wavelength range may be greater than about 70%. In some embodiments, the second region may have a substantially low transmission in the predetermined first wavelength range. For example, the average optical transmittance of the second region 240 in the predetermined first wavelength range may be less than about 10%. In some cases, the second region 240 may have a substantially high transmission in the predetermined first wavelength range. For example, the average optical transmittance of the second region in the predetermined first wavelength range may be greater than about 70%.

In some cases, as shown in FIG. 2, an LCF 200 includes a plurality of spaced apart first regions 230 and a second region 240. Each first region 230 may have a width W and a height H and an aspect ratio H/W that is at least 1 (H/W≥1) or H/W≥2, or H/W≥5, or H/W≥10, or H/W≥20. Each first region 230 may have a substantially high transmission in a predetermined first wavelength range and a substantially low transmission in a predetermined non-overlapping second wavelength range. The second region 240 may have substantially high transmission in each of the predetermined first and second wavelength ranges.

Figure 6:
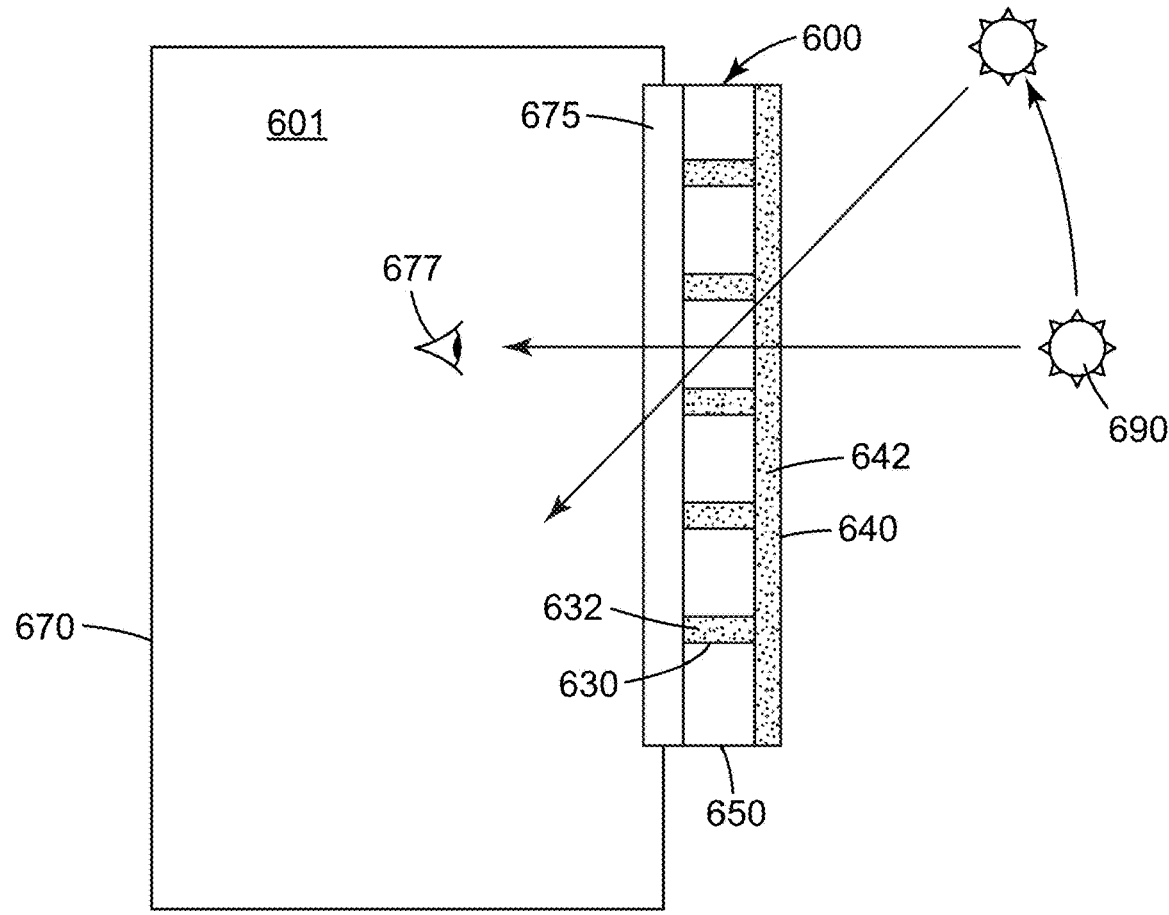
FIG. 6 is a schematic cross-sectional view of an exemplary light control film applied to a window of an enclosure, such as a building, a house or a vehicle.

In some cases, the light control films (LCFs) disclosed herein may be part of an optical communication system including an optical construction combined with, for example, a window as shown in FIG. 6. In this example, the LCF 600 is a part of an optical construction 601 with a natural light source such as sun light 690. In particular, FIG. 6 shows an exemplary application of a disclosed LCF applied to a window to an enclosure, such as a building, a house or a vehicle. LCF 600 may be disposed on a window substrate 675 of a building, a house, a car or any enclosure 670. The LCF 600 includes an optical film 650 that includes a plurality of spaced apart first regions 630 and a second region 640 adjacent at least a portion of at least one first region 630. The first regions 630 may be filled at least partially with a first material 632 and the second region 640 may include a second material 642. The first material 632 and the first region 630 may be any suitable material and shape such that each first region 630 has an average optical transmittance of greater than about 50%, or 60%, or 70%, or 80%, or 90% in a first wavelength range from about 400 nm to about 700 nm and an average optical transmittance of less than about 10% in a non-overlapping second wavelength range from about 700 nm to about 1200 nm. The second material 642 and the second region 640 may be any suitable material and shape such that the second region 540 has an average optical transmittance of greater than about 30%, or 40%, or 50%, or 60%, or 70%, or 80%, or 90% in each of the predetermined first and second wavelength ranges. In addition, the second region 640 may have an average optical transmittance of less than about 10% in a wavelength range from about 350 nm to about 400 nm. In some cases, the wavelength separation distance between the non-overlapping first and second wavelength ranges may be at least 5 nm, or at least 10 nm, or at least 15 nm, or at least 20 nm. In some cases, the LCF 600 has a viewing angle 2θv of less than about 40 degrees for at least one wavelength in the second wavelength range. In this example, when sun light 690 is incident on the front surface of the LCF 600, the second material 642 of the second region 640 absorbs or/and reflects at least a part of light incident having wavelengths in a range from about 350 nm to 400 nm (the ultraviolet light range) substantially independent of the incidence angle of the light 690. The second region 640 is sufficiently absorbing or/and reflecting light such that the transmission of the ultraviolet light passing through the second region 640 and exiting the LCF 600 is uniform and desirably, less than about 10% and substantially independent of the incidence angle of the light. In some cases, in order to achieve the transmission of the ultraviolet light passing through the second region 640 and exiting the LCF 600 than about 10%, thickness or size of the second materials 642 may be increased, or the second region 640 may include multiple layers of the second materials 642, or the multiple layers of the second materials 642 may be provided on at least one of the first surface 610 and second surface 620, or either the first or second surfaces 610, 620 may include multiple layers of the second materials 642, or the concentration of the second materials 642 may be increased. In some cases, the transmission in the ultraviolet light range may be less than 10% by providing scattering particles in and/or on the optical film 650. At the same time, the second region 640 has an average optical transmittance of greater than about 30%, or 40%, or 50%, or 60%, or 70%, or 80%, or 90% in each of the range from about 400 nm to about 700 nm and from about 700 nm to about 1200 nm. The transmission of the infrared light (from about 700 nm to about 1200 nm) by the first regions 630 vary as a function of the incidence angle of the light. In particular, when the sun light 690 is incident perpendicularly to the LCF 600, the infrared light and the visible light may both be transmitted through the optical film 650. However, as the incidence angle of the light from the sun 690 increases, the amount of the infrared light transmitted through the LCF 600 decreases until the incidence angle reaches the viewing angle 2θv from which point on substantially all the infrared light is blocked by the first material 632. At the same time, first regions 630 transmit substantially all light in the visible light range. Therefore, in the exemplary optical communication system of FIG. 6, substantially all visible light may be transmitted by the LCF 600, but the ultraviolet light range may not be transmitted by the LCF 600 or only a restricted amount of the ultraviolet light range, desirably less than about 10% of the ultraviolet wavelength range, may be transmitted by the LCF 600. And regarding the infrared light range of the sun light 690, the transmission of the infrared light passing through the LCF 600 is a function of the incidence angle. That is, during the morning hours when the infrared portion of the sun light 690 is relatively small and the sun light 690 is incident on the window at normal incidence angle, most of the infrared light may be transmitted by the LCF 600. On the other hand, close to noon, when the infrared portion of the sun light 690 is relatively large and the incident angle of the sun light 690 is increased close to or beyond the viewing angle 2θv of the LCF 600, very little of the incident infrared light is transmitted by the LCF 600 and finally blocked so that the viewer or resident 677 inside of the building or house 670 may not be exposed to the hot infrared light. And also, the LCF 600 may prevent household items from being damaged due to exposure to the ultraviolet light of the sun light 690 regardless of the incidence angle and, at the same time, the viewer or resident 677 may not become hot from exposure to the infrared light, while the visible light may be transmitted through the LCF 600 such that the sun light 690 may effectively be used to provide lighting to the enclosure 670.

In some embodiments, as shown in FIG. 2, an LCF 200 includes a plurality of spaced apart first regions 230 and a second region 240. Each first region 230 may have a width W and a height H and an aspect ratio H/W that is at least 1 (H/W≥1) or H/W≥2, or H/W≥5, or H/W≥10, or H/W≥20. Each first region 230 may have a substantially low transmission in a predetermined first wavelength range and a substantially high transmission in a predetermined non-overlapping second wavelength range. Each second region 240 may have substantially low transmission in each of the predetermined first and second wavelength ranges.

In other cases, as shown in FIG. 2, an LCF 200 includes a plurality of spaced apart first regions 230 and a second region 240. Each first region 230 may have a width W and a height H and an aspect ratio H/W that is at least 1 (H/W≥1) or H/W≥2, or H/W≥5, or H/W≥10, or H/W≥20. Each first region 230 may have a substantially high transmission in a predetermined first wavelength range and a substantially low transmission in a predetermined non-overlapping second wavelength range. The second region 240 may have substantially low transmission in each of the predetermined first and second wavelength ranges.

In some cases, as shown in FIG. 2, an LCF 200 includes a plurality of spaced apart first regions 230 and a second region 240. Each first region 230 may have a width W and a height H and an aspect ratio H/W that is at least 1 (H/W≥1) or H/W≥2, or H/W≥5, or H/W≥10, or H/W≥20. Each first region 230 may have a substantially low transmission in a predetermined first wavelength range and a substantially high transmission in a predetermined non-overlapping second wavelength range. The second region 240 may have substantially high transmission in each of the predetermined first and second wavelength ranges.

Figure 7:
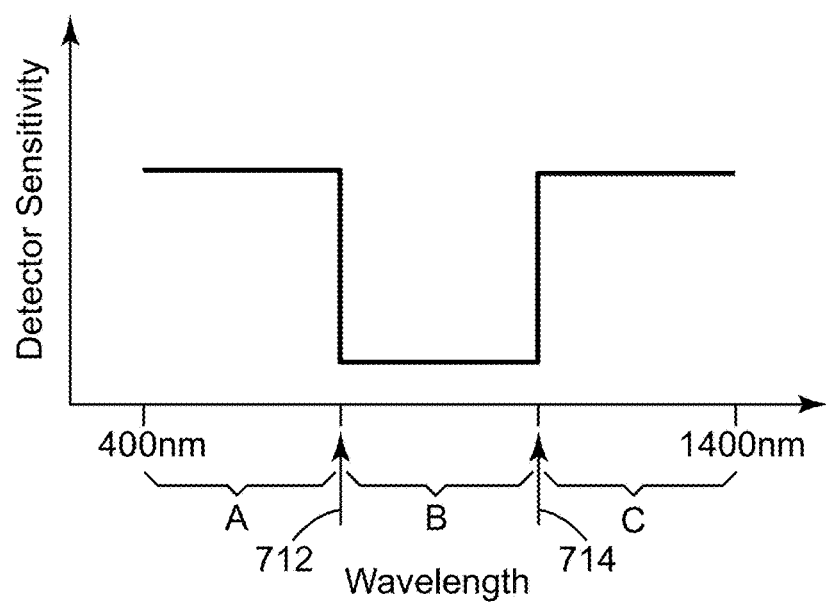
FIG. 7 is a schematic plot of transmission of a light control film vs. wavelength.

In further examples as shown in FIG. 7, each first region of a disclosed LCF may have a substantially high transmission in a predetermined first wavelength range "A", a substantially low transmission in a predetermined second wavelength range "B", and a substantially high transmission in a predetermined third wavelength range "C", where the second wavelength range B is disposed between the first and third wavelength ranges A and, respectively. In some cases, the second wavelength range B is about 20 nm wide from a first wavelength 712 to a second wavelength 714 and centered on a laser visible emission wavelength, the first wavelength range A is from about 400 nm to about the first wavelength 712, and the third wavelength range C is from about the second wavelength 714 to about 1400 nm. The laser visible emission wavelength may be at least one of 442 nm, 458 nm, 488 nm, 514 nm, 632.8 nm, 980 nm, 1047 nm, 1064 nm, and 1152 nm. In other examples, the laser visible emission wavelength is in a range from about 416 nm to about 1360. In further examples, the LCF further may include a plurality of spaced apart second regions alternating with the plurality of first regions and each second region may have a substantially high transmission in each of the predetermined first, second and third wavelength ranges. In other example, each second region may have a substantially low transmission in either/both the predetermined first or/and third wavelength ranges. In some cases, the LCF has a viewing angle 2θv of less than about 60 degrees, or 50 degrees, or 40 degrees, or 30 degrees, or 20 degrees in the predetermined second wavelength range.

Figure 8:
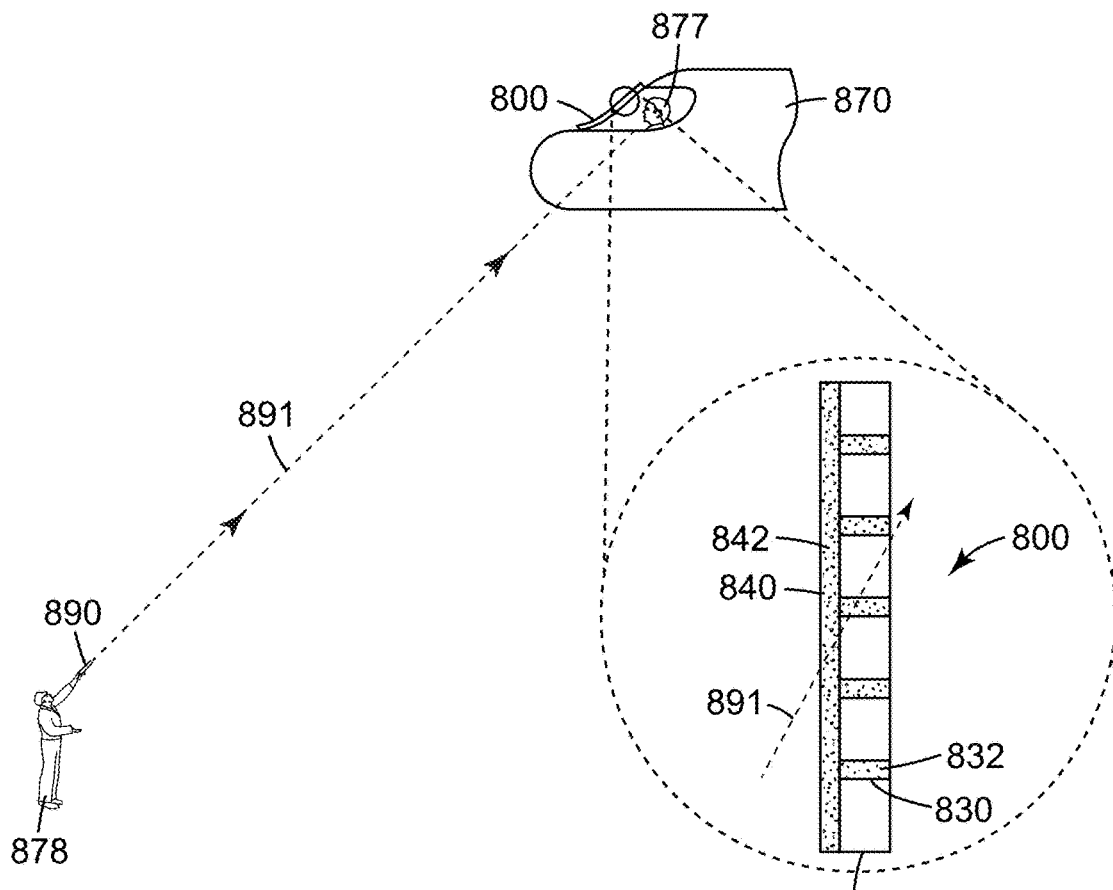
FIG. 8 is a schematic view of an exemplary application where a light control film is applied to a plane or an aircraft.

In another exemplary application, the LCFs disclosed herein may be a part of an optical communication system with a separate light source such as laser light source as shown in FIG. 8. In particular, FIG. 8 shows an exemplary application where a LCF is applied to a plane or an aircraft laser strike defense system to block an incoming or incident light in a predetermined wavelength range. An LCF 800 may be attached to, for example, a plane, an airplane or aircraft 870, etc. and desirably, attached to a surface (such as a window) of the plane, airplane or aircraft 870. The LCF 800 includes an optical film 850 that includes a plurality of spaced apart first regions 830 and a second region 840 adjacent at least a portion of at least one of the first regions 830. The first regions 830 may be filled at least partially with a first material 832 and the second region 840 includes a second material 842. The first material 832 or the second material 842 may be any suitable material such that the first material 832 absorbs or/and reflects in at least a part of visible light range that includes the laser light 891 and the second material 842 absorbs or/and reflects in at least a part of at least one of ultraviolet light and infrared light ranges that include the laser light 891. More desirably, the second material 842 may absorb or/and reflect in both ultraviolet and infrared wavelength ranges in this example. When laser light 891 is incident on the LCF 800, the second material 842 of the second region 840 absorbs or/and reflects at least a part of ultraviolet light and infrared wavelength ranges regardless of the incidence angle of the light 891. Furthermore, the second region 840 transmits in a range of the visible wavelengths that include the laser light 891 wavelength, but the transmission of the visible light through the first regions 830 vary as a function of an incidence angle of the light. When the light is incident perpendicularly to the surface of the LCF 800, the visible light can be transmitted through the optical film 850. However, outside viewing angle, 2θv (refer to FIG. 2), the visible light is blocked by the first material 832 in the first regions 830. Therefore, when using the LCF 800 on the plane or aircraft 870, the visible light from the laser light 891 within the viewing angle 2θv can be transmitted by the LCF 800 but the ultraviolet light and the infrared light from the laser light 891 may not be transmitted by the LCF 800 or only a restricted amount of the ultraviolet light and infrared light, desirably less than about 10% the ultraviolet light and infrared light respectively may be transmitted by the LCF 800. And for the visible light, it can be transmitted by the LCF 800 as a function of an incidence angle and a wavelength of the light. Laser striker 878 may attack the plane or aircraft 870, for example, using a green laser 890 in order to obstruct a view of a pilot 877. Normally, the wavelength of the green color is about from 495 nm to 570 nm. Therefore, the LCF 800 with the first material 832 that absorbs or/and reflects the range of the wavelength from 495 nm to 570 nm of the light, so that the pilot 877 on the plane or aircraft 870 is not affected by the green laser attack from the laser striker 878 on the ground.

Figure 9:
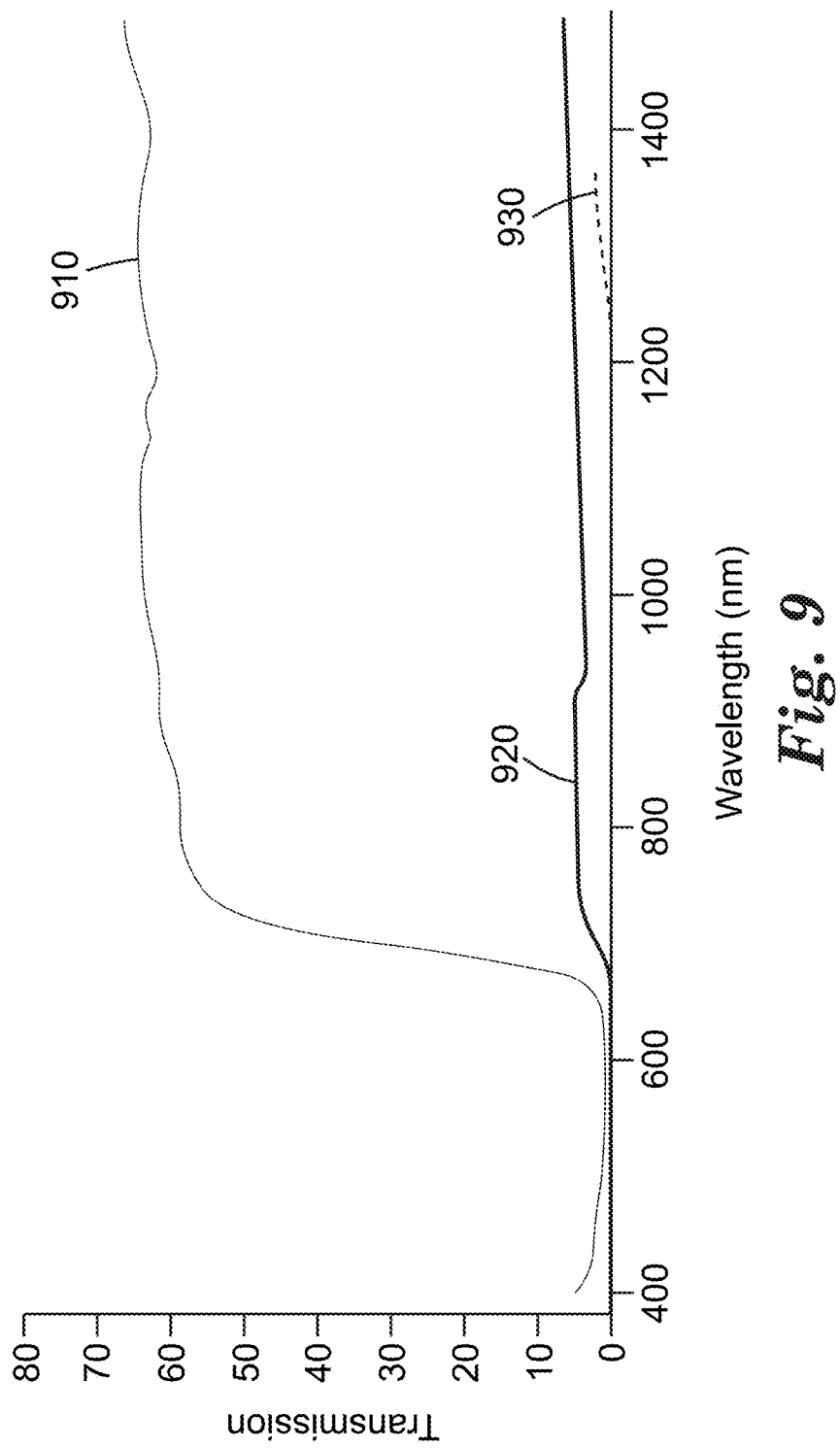
FIG. 9 is a plot of transmission vs. wavelength of an exemplary light control film.

FIG. 9 is a plot of transmission vs. wavelength for the exemplary disclosed optical films that may be useful in forming light control films. In some embodiments, an LCF includes a plurality of first and second regions, such that for light incident normally to a plane of the LCF, an average optical transmittance of the LCF may be less than about 10% in a predetermined first wavelength range having shorter wavelengths, and an average optical transmittance of the LCF may be greater than about 50% in a predetermined second wavelength range having longer wavelengths. And for light incident at or greater than about 30 degrees from the plane of the LCF, an average optical transmittance of the LCF may be less than about 20% in each of the predetermined first and second wavelength ranges. In exemplary cases, the predetermined first wavelength range may be from about 400 nm to about 650 nm, and the predetermined second wavelength range may be from about 750 nm to about 1500 nm. In some cases, the second region includes a plurality of spaced apart second region segments alternating with the plurality of first regions. In some cases, the light control film includes a major microstructured first surface having a plurality of alternating ribs and channels, where each channel is at least partially filled with a first material to form one of the first regions in the plurality of spaced apart first regions. In some cases, the second region includes a plurality of second region segments, and each rib incudes one of the second region segments. In some cases, the second region is disposed on a major surface of the light control film and extend across and cover at least some of the first regions. In some cases, the average optical transmittance of the first regions in the predetermined second wavelength range is less than about 20%, or less than about 15%, or less than about 10%, or less than about 5%, or less than about 1%. In some cases, the average optical transmittance of the second region in the predetermined first wavelength range is less than about 20%, or less than about 15%, or less than about 10%, or less than about 5%, or less than about 1%. In some cases, the average optical transmittance of the second region in the predetermined second wavelength range is greater than about 40%, or greater than about 50%, or greater than about 60%, or greater than about 70%, or greater than about 80%, or greater than about 90%. In some cases, for light incident normally to the plane of the light control film, the average optical transmittance of the light control film is less than about 5%, or less than about 1%, in the predetermined first wavelength range. In some cases, for light incident normally to the plane of the light control film, the average optical transmittance of the light control film is greater than about 55%, or 60%, in the predetermined second wavelength range.

Figure 10:
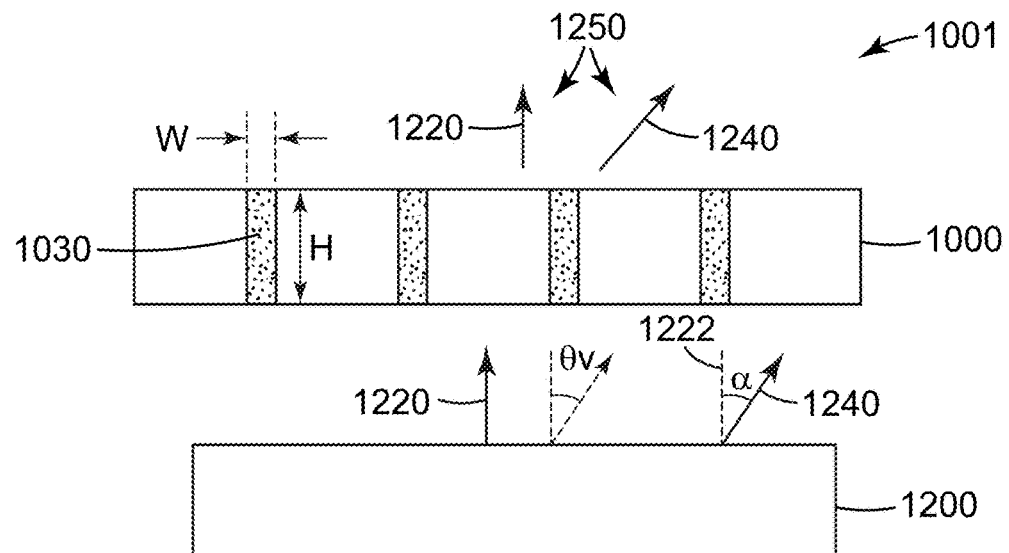
FIG. 10 is a schematic of an exemplary optical communication system including a light control film and a light source.
Figure 10A:
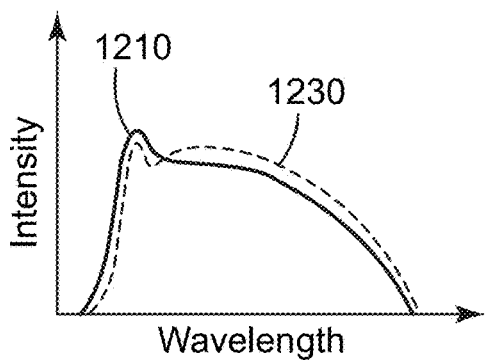
FIG. 10A is a schematic plot of spectral profile of light emitted by the light source of FIG. 10 along different directions.
Figure 10B:
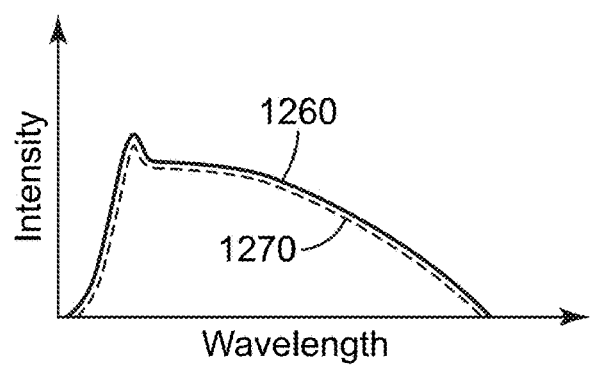
FIG. 10B is a schematic plot of spectral profile of light transmitted by the light control of FIG. 10 along different directions.
Figure 10C:
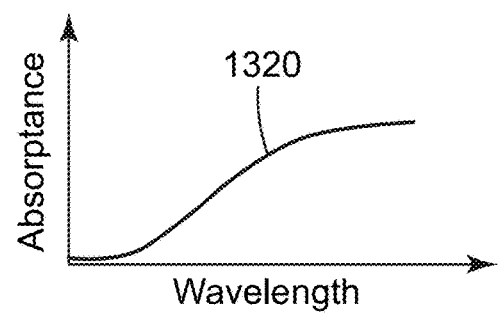
FIG. 10C is a schematic plot of absorbance of portions of the light control film of FIG. 10.

Furthermore, as shown in FIG. 9, an LCF includes a plurality of first and second regions, such that plot 910 is the optical transmission of the LCF for normally incident light, plot 920 is the optical transmission of the LCF for 30 degree incident light, and plot 930 is the optical transmission of the LCF for 60 degree incident light, where all three plots are shown as a function of the wavelength of the incident light. Hence, the average optical transmission of the LCF is less than about 10%, or less than about 7%, or less than about 5% for all angles of incidence for wavelengths from about 400 nm to about 620 nm, or 610 nm, or 600 nm. Furthermore, for the wavelength range from about 700 nm, or about 710 nm, or about 720 nm to about 1500 nm, the average optical transmission of the LCF changes from about 60% to about 5% when the angle of incidence changes from zero degree to about 30 degrees, and the average optical transmission of the LCF changes from about 60% to about 2%, or about 1% when the angle of incidence changes from zero degree to about 60 degrees. Hence, when an angle of incidence of light incident on the LCF changes from about 90 degrees to about 60 degrees relative to the plane of the LCF (or, about zero degree to about 30 degrees from a line normal to the plane of the LCF), an average optical transmittance of the LCF may change by less than about 10% in a predetermined first wavelength range having shorter wavelengths and greater than about 40% in a predetermined second wavelength range having longer wavelengths. In some cases, the average optical transmittance of the first regions in the predetermined second wavelength range is less than about 20%, or less than about 15%, or less than about 10%, or less than about 5%, or less than about 1%. In some cases, the average optical transmittance of the second region in the predetermined first wavelength range is less than about 20%, or less than about 15%, or less than about 10%, or less than about 5%, or less than about 1%. In some cases, the average optical transmittance of the second region in the predetermined second wavelength range is greater than about 40%, or greater than about 50%, or greater than about 60%, or greater than about 70%, or greater than about 80%, or greater than about 90%. In some cases, when the angle of incidence of light incident on the light control film changes from about 90 degrees to about 60 degrees relative to the plane of the light control film, the average optical transmittance of the light control film changes by less than about 5%, in the predetermined first wavelength range. In some cases, when the angle of incidence of light incident on the light control film changes from about 90 degrees to about 60 degrees relative to the plane of the light control film, the average optical transmittance of the light control film changes by less than about 1% in the predetermined first wavelength range. In some cases, when the angle of incidence of light incident on the light control film changes from about 90 degrees to about 60 degrees relative to the plane of the light control film, the average optical transmittance of the light control film changes by greater than about 55%, or 60%, in the predetermined second wavelength range. The disclosed light control films (LCFs) may advantageously be utilized in various applications. For example, in some cases, the disclosed LCFs may improve angular uniformity of the spectral profile of a light source. For example, FIG. 10 illustrates a light source system 1001 for improving the emission spectral profile of a light source along different emission directions. In particular, FIG. 10 shows a light source 1200 that is configured to emit light having different spectral profiles along different directions. For example, referring FIGS. 10A, 10B and 10C, light source 1200 emits light having a first spectral profile 1210 along a first direction 1220 and a second spectral profile 1230 along a different second direction 1240. In the exemplary light source system 1001, first direction 1220 is normal to the plane of the light source. In general, the first and second directions may be any two directions along which the emitted light may have different spectral profiles. The light source system 1001 further includes a LCF (LCF) 1000 disposed on light source 1200 for improving the angular spectral profile uniformity of the light source. LCF 1000 receives light emitted by light source 1200 and transmits the received light. LCF 1000 may be any LCF disclosed herein. For example, LCF 1000 includes a plurality of spaced apart first regions 1030. Each first region has a width W and a height H, where, in some cases, H/W≥1, or H/W≥2, or H/W≥5, or H/W≥10, or H/W≥20. In general, the orientation and absorbing properties of the first regions 1030 are at least some of the factors that improve the angular spectral profile uniformity of light transmitted by the LCF 1000. Other factors may include, for example, the viewing angle 2θv of the LCF which may depend on, for example, the pitch of the first regions 1030 and the ratio H/W. In some cases, first regions 1030 are oriented relative to first direction 1220 and second direction 1240 and the spectral absorbance profile 1320 (refer to FIG. 10C) of the first regions 1030 is so that when light that is emitted by the light source 1200 is transmitted by the LCF 1000, the transmitted light has a third spectral profile 1260 along the first direction 1220 and a fourth spectral profile 1270 along the second direction 1240, where the difference between the third and fourth spectral profiles 1260 and 1270 is less than the difference between the first and second spectral profiles 1210 and 1230. For example, in some cases, the difference between the third and fourth spectral profiles 1260 and 1270 is at least 5%, or at least 10%, or at least 15%, or at least 20%, or at least 30%, or at least 40%, or at least 50% less than the difference between the first and second spectral profiles 1210 and 1230. In some cases, such as when first direction 1220 is perpendicular to the plane of light source 1200, the spectral profile of light incident on the LCF 1000 along the first direction 1220 may remain unchanged upon transmission by the LCF. In such cases, first spectral profile 1210 may be substantially equal to third spectral profile 1260. Furthermore, the first regions 1030 may selectively absorb light propagating along second direction 1240 so that spectral profile 1230 changes upon transmission to spectral profile 1270 more closely matching third spectral profile 1260. In some cases, LCF 1000 improves the angular spectral profile uniformity of light source 1200 by each first region 1030 selectively absorbing light within each of the first and second spectral profiles 1210 and 1230. For example, in cases, where neither first nor second direction 1220, 1240 is perpendicular to the plane of light source 1200 or LCF 1000, each first regions 1030 may selectively absorb light within each of the first and second spectral profiles 1210 and 1230. In some cases, second direction 1240 makes an angle α with a line 1222 that is normal to the plane of light source 1200. In some cases, angle α is greater than θv where 2θv is the viewing angle of LCF 1000. In such cases, at least a majority of light rays emitted by light source 1200 along first direction 1220 pass through first regions 1030 and, as a result, may be selectively absorbed. Such selective absorption may improve the angular color uniformity of the light source 1200. In some cases, light emitted from the light source 1200 and propagating along first direction 1220 has a first set of color coordinates, and light propagating along second direction 1240 has a second set of color coordinates, wherein light transmitted by LCF 1000 and propagating along the first direction 1220 has a third set of color coordinates and propagating along the second direction 1240 has a fourth set of color coordinates, where the difference between the third and fourth sets of color coordinates is less than the difference between the first and second sets of color coordinates. For example, in some cases, the first set of color coordinates are u1' and v1', the second set of color coordinates are u2' and v2', the third set of color coordinates are u3' and v3', and the fourth set of color coordinates are u4' and v4'. In such cases, the absolute value of each of (u4'-u3') and (v4'-v3') may be less than 5%, or less than 10%, or less than 15%, or less than 20%, or less than 30%, or less than 40%, or less than 50% of each of the corresponding (u1'-u2') and (v1'-v2').

Figure 11:
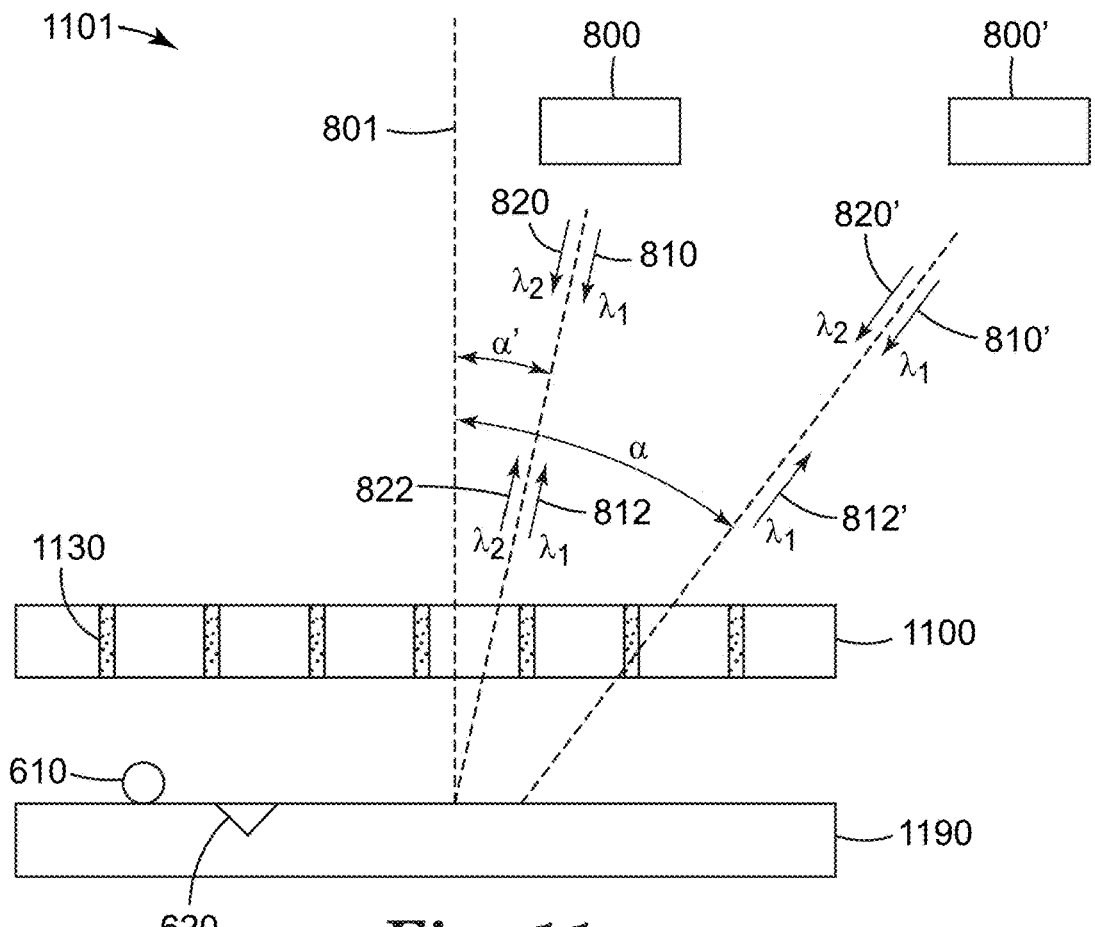
FIG. 11 is a schematic cross-sectional view of an exemplary optical communication system including a light control film combined with a retroreflector.

In some cases, the disclosed light control films (LCFs) may be utilized in combination with retroreflectors. For example, FIG. 11 shows a retroreflective system 1101 that includes a retroreflective sheet 1190 for retroreflecting light, and a LCF 1100 disposed on the retroreflective sheet 1190. In general, retroreflector sheet 1190 is configured to retroreflect light for a range of incident wavelengths and angles. For example, retroreflector sheet 1190 may be configured to retroreflect light for different incident wavelengths $\lambda_1$ and $\lambda_2$ and different incident angles α and α'. The addition of LCF 1100 results in system 1101 having modified retroreflective properties. For example, for a larger angle α and a smaller angle α', the viewing angle 2θv of LCF 1100 may be such that for the smaller incident angle α', LCF 1100 substantially transmits light at both wavelengths $\lambda_1$ and $\lambda_2$, but for the larger incident angle α, LCF may substantially transmit light having wavelength $\lambda_1$ and substantially absorb light having wavelength $\lambda_2$. For example, in some cases, the viewing angle 2θv of LCF 1100 may be greater than α' and less than α. As another example, retroreflective system 1101 is so configured that for a first wavelength $\lambda_1$, lights 810 and 810' incident on LCF 1100 at corresponding first and second angles of incidence α' and α, are both retroreflected as respective retroreflected lights 812 and 812'. Furthermore, for a second wavelength $\lambda_2$, light 820 incident on the LCF at the first incidence angle α' is retroreflected at retroreflected light 822, but light 820' incident on the LCF at the second incidence angle α is not retroreflected. In such cases, light 820' is absorbed by LCF 1100 when it is first incident on the LCF and, in some cases, after it is partially transmitted by the LCF and retroreflected by the retroreflective sheet. In some cases, LCF 1100 includes a larger first viewing angle for the first wavelength and a smaller viewing angle for the second wavelength. In some cases, the first angle of incidence α' is substantially equal to zero relative to a line 801 normal to a plane of the LCF 1100. In some cases, retroreflective sheet 1190 includes microsphere beads 610 for retroreflecting light. In some cases, retroreflective sheet 1190 includes corner cubes 620 for retroreflecting light. In some cases, LCF 1100 includes a plurality of spaced apart first regions 1130, where each first region 1130 has a substantially low transmission at the second wavelength $\lambda_2$, but not at the first wavelength $\lambda_1$.

In some cases, the light control film (LCF) may be used as part of an optical communication system having a sensor, more specifically, an IR sensor in order to improve signal to noise performance and enable improved directional sensing. In this example, the first material is spectrally selective in at least a part of infrared light range and in some cases, the second material may be spectrally selective in at least a part of at least one of ultraviolet light and visible light ranges. More desirably, the second material is spectrally selective in both r ultraviolet light and visible light ranges. When using the LCF, noises like ultraviolet light and visible light from the IR sensor are absorbed through the second material regardless of the incidence angle of light. The transmission of the ultraviolet light and visible light from a light source passing through the second region is uniform and desirably, less than about 10% regardless of the incidence angle of the light. However, the second region may transmit a range of the infrared light from light source but the transmission of the infrared light through the first regions vary as a function of an incidence angle of the light. When light is incident perpendicularly to the surface of the LCF, the infrared light may be transmitted through the optical film. However, outside the viewing angle, 2θv, the infrared light is blocked by the first material in the first regions. Therefore, the disclosed system provides an IR sensor with substantially reduced noise and substantially improved directional sensing.

Figure 12:
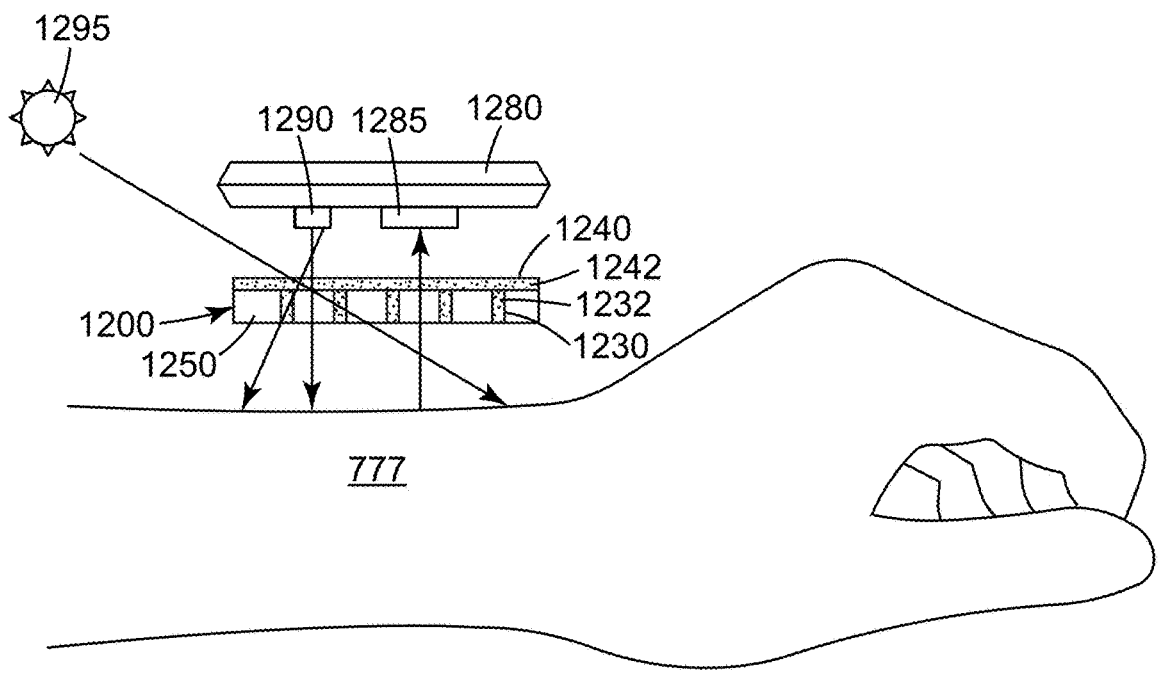
FIG. 12 is a schematic cross-sectional view of an exemplary wearable optical communication system including a light control film and a wrist watch with a pulse sensor.

In another case, the LCF can be used in a part of an optical communication system with a sensor, more specifically a pulse sensor applied to a wrist watch as shown in FIG. 12. In particular, FIG. 12 shows an exemplary application of an LCF applied to a wrist watch with a pulse sensor. An LCF 1200 may be attached to a wearable wrist watch 1280 or any wearable device and desirably, attached to a surface of the wearable watch 1280. The LCF 1200 includes an optical film 1250 that includes a plurality of first regions 1230 and a second region 1240 adjacent at least a portion of at least one first regions 1230. The first regions 1230 may be filled at least partially with a first material 1232 and the second region 1240 may include a second material 1242. The first material 1232 or the second material 1242 may be any suitable material such that the first material 1232 is spectrally selective in at least a part of visible light range from the light source, for example, LED 1290 and the second material 1242 is spectrally selective in at least a part of at least one of ultraviolet light and infrared light ranges from the LED 1209. More desirably, the second material 1242 is spectrally selective in both ranges in the ultraviolet light and infrared light ranges. When using the LCF 1200, noises like ultraviolet light and infrared light from the perspective of a pulse sensor 1285 are absorbed through the second material 1242 regardless of the incidence angle of the light from light source such as sun light 1295 or LED 1290. The transmission of the ultraviolet light and infrared light from the light source passing through the second region 1240 is uniform and desirably, less than about 10%, regardless of the incidence angle of the light. However, the second region 1240 transmits a range of the visible light from LED 1290 but the transmission of the visible light through the first regions 1230 varies as a function of the incidence angle of the light. When the light from LED 1290 is incident perpendicularly on the surface of the LCF 1200, the visible light may be transmitted through the optical film 1250. However, the first material 1232 may block or decrease the sun light 1295 or ambient visible light from other light sources that are incident with relatively high incidence angle to the wrist 777 of the person wearing the device so that the LCF 1200 may improve signal (mainly visible light from LED that is incident within a viewing angle) to noise (for example, ultraviolet light or infrared light or ambient visible light from, for example, sunlight, other ambient light source that is incident outside viewing angle) ratio. In some cases, the sensor may be a sensor in a camera or camera system. In some cases, a camera includes the sensor.

The following is a list of exemplary embodiments of the present description.

Embodiment 1 is a light control film that includes a plurality of spaced apart first regions, each first region having a substantially low transmission in one or two of a first wavelength range from about 300 nm to about 400 nm, a second wavelength range from about 400 nm to about 700 nm, and a third wavelength range from about 700 nm to about 1200 nm, and a substantially high transmission in remaining wavelength ranges, wherein the light control film includes a first viewing angle of less than about 70 degrees along a predetermined first direction.

Embodiment 2 is the light control film of Embodiment 1 having a second viewing angle of less than about 70 degrees along an orthogonal predetermined second direction different from the first viewing angle.

Embodiment 3 is the light control film of Embodiment 1 including a major micro structured first surface having a plurality of alternating ribs and channels, each channel at least partially filled with a first material to form one of the first regions in the plurality of spaced apart first regions.

Embodiment 4 is the light control film of Embodiment 3, wherein each rib has a substantially high transmission in each wavelength range the first regions have a substantially low transmission in.

Embodiment 5 is the light control film of Embodiment 3, wherein each rib has a substantially low transmission in at least one wavelength range the first regions have a substantially high transmission in.

Embodiment 6 is the light control film of Embodiment 1 further including a plurality of second regions alternating with the plurality of first regions, each second region having a substantially high transmission in each wavelength range the first regions have a substantially low transmission in.

Embodiment 7 is the light control film of Embodiment 1 further including a plurality of second regions alternating with the plurality of first regions, each second region having a substantially low transmission in at least one wavelength range the first regions have a substantially high transmission in.

Embodiment 8 is the light control film of Embodiment 6 or 7, wherein each second region is disposed on a major surface of the light control film.

Embodiment 9 is the light control film of Embodiment 1 further including a second region extending across and covering at least some of the first regions, the second region having a substantially low transmission in at most one, but not all, wavelength regions the first regions have a substantially high transmission in.

Embodiment 10 is the light control film of Embodiment 1, wherein the first wavelength range is from about 350 nm to about 400 nm.

Embodiment 11 is the light control film of Embodiment 1, wherein the first wavelength range is from about 350 nm to about 380 nm.

Embodiment 12 is the light control film of Embodiment 1, wherein the second wavelength range is from about 400 nm to about 460 nm.

Embodiment 13 is the light control film of Embodiment 1, wherein the second wavelength range is from about 470 nm to about 550 nm.

Embodiment 14 is the light control film of Embodiment 1, wherein the third wavelength range is from about 800 nm to about 1000 nm.

Embodiment 15 is the light control film of Embodiment 1, wherein the third wavelength range is from about 820 nm to about 1200 nm.

Embodiment 16 is the light control film of Embodiment 1, wherein the third wavelength range is from about 885 nm to about 1200 nm.

Embodiment 17 is the light control film of Embodiment 1, wherein the third wavelength range is from about 920 nm to about 1200 nm.

Embodiment 18 is a light control film that includes a major microstructured first surface having a plurality of alternating ribs and channels, each channel at least partially filled with a first material, each channel including a width W and a height H, H/W≥1, each rib having a second material, wherein an absorption of at least one of the first and second materials varies as a function of wavelength in a range from about 300 nm to about 1200.

Embodiment 19 is the light control film of Embodiment 18, wherein the absorption of each of the first and second materials varies as a function of wavelength in a range from about 400 nm to about 1200.

Embodiment 20 is a light control film including a plurality of spaced apart first regions and a second region, each first region having a substantially low transmission in a first wavelength range from about 700 nm to about 1200 nm, the second region having a substantially low transmission in a second wavelength range from about 300 nm to about 400 nm.

Embodiment 21 is the light control film of Embodiment 20 including a major microstructured first surface having a plurality of alternating ribs and channels, each channel at least partially filled with a first material to form one of the first regions in the plurality of spaced apart first regions.

Embodiment 22 is the light control film of Embodiment 21, wherein the second region includes a plurality of second region segments, each rib including one of the second region segments.

Embodiment 23 is the light control film of Embodiment 20, wherein the second region is disposed on a major surface of the light control film.

Embodiment 24 is the light control film of Embodiment 20, wherein the second region extends across and covers at least some of the first regions.

Embodiment 25 is a light control film including a plurality of spaced apart first regions and a second region, each first region having a substantially low transmission in at least one of a first wavelength range from about 300 nm to about 400 nm, a second wavelength range from about 400 nm to about 700 nm, and a third wavelength range from about 700 to about 1200 nm, the second region having a substantially low transmission in at least one of the at least one of the three wavelength ranges each first region has substantially low transmission in.

Embodiment 26 is the light control film of Embodiment 25, wherein each first region and the second region have substantially low transmission in a same two of the three wavelength ranges.

Embodiment 27 is the light control film of Embodiment 25 including a major microstructured first surface having a plurality of alternating ribs and channels, each channel at least partially filled with a first material to form one of the first regions in the plurality of spaced apart first regions.

Embodiment 28 is the light control film of Embodiment 27, wherein the second region includes a plurality of second region segments, each rib including one of the second region segments.

Embodiment 29 is the light control film of Embodiment 25, wherein the second region is disposed on a major surface of the light control film.

Embodiment 30 is the light control film of Embodiment 25, wherein the second region extends across and covers at least some of the first regions.

Embodiment 31 is a light control film including a plurality of spaced apart first regions and a second region, each first region having a substantially high transmission in a first wavelength range from about 300 nm to about 400 nm and a substantially low transmission in a second wavelength range from about 400 nm to about 700 nm, the second region having a substantially high transmission in each of the first and second wavelength regions.

Embodiment 32 is the light control film of Embodiment 31 including a major microstructured first surface having a plurality of alternating ribs and channels, each channel at least partially filled with a first material to form one of the first regions in the plurality of spaced apart first regions.

Embodiment 33 is the light control film of Embodiment 32, wherein the second region includes a plurality of second region segments, each rib including one of the second region segments.

Embodiment 34 is the light control film of Embodiment 31, wherein the second region is disposed on a major surface of the light control film.

Embodiment 35 is the light control film of Embodiment 31, wherein the second region extends across and covers at least some of the first regions.

Embodiment 36 is the light control film of Embodiment 31, wherein each first region and the second region have substantially high transmissions in a third wavelength range from about 700 nm to about 1200 nm.

Embodiment 37 is the light control film of Embodiment 31, wherein each first region has a substantially low transmission region in a third wavelength range from about 700 nm to about 1200 nm, and the second region has a substantially high transmission region in the third wavelength range.

Embodiment 38 is a detector system, including:
a detector sensitive to wavelengths in a detection wavelength range; and
a light control film disposed on the detector and including a plurality of alternating first and second regions, each first region having a width W and a height H, H/W≥1, each first region having a substantially low transmission in a first portion of the detection wavelength range and a substantially high transmission in a remaining portion of the detection wavelength range, each second region having a substantially high transmission in the detection wavelength range.

Embodiment 39 is the detector system of Embodiment 38, wherein the detection wavelength range is from about 800 to about 1600 and the first portion of the detection wavelength range is from about 900 nm to about 1100 nm.

Embodiment 40 is the detector system of Embodiment 38, wherein a viewing angle of the light control film in the first portion of the detection wavelength range is less than about 70 degrees along a first direction.

Embodiment 41 is the detector system of Embodiment 38, wherein the light control film includes a major microstructured first surface having a plurality of alternating ribs and channels, each channel at least partially filled with a first material to form one of the first regions, each rib including a second material and forming one of the second regions.

Embodiment 42 is the detector system of Embodiment 38, wherein H/W≥5.

Embodiment 43 is the detector system of Embodiment 38, wherein H/W≥10.

Embodiment 44 is a light control film including a plurality of spaced apart first regions and a second region, each first region having a width W and a height H, H/W≥1, each first region having substantially low transmissions in each of non-overlapping predetermined first and second wavelength ranges, the second region having a substantially low transmission in the predetermined second wavelength range.

Embodiment 45 is the light control film of Embodiment 44, wherein the predetermined first wavelength range includes shorter wavelengths and the predetermined second wavelength range includes longer wavelengths.

Embodiment 46 is the light control film of Embodiment 44, wherein the predetermined first wavelength range is from about 400 nm to about 700 nm.

Embodiment 47 is the light control film of Embodiment 44, wherein the predetermined second wavelength range is from about 700 nm to about 1200 nm.

Embodiment 48 is the light control film of Embodiment 44, wherein an average optical transmittance of each first region in the predetermined first wavelength range is less than about 25, or 15%, or 10%, or 5%, or 1%, or 0.1%, or 0.01%, or 0.001, or 0.0001%.

Embodiment 49 is the light control film of Embodiment 44, wherein an average optical transmittance of each first region in the predetermined second wavelength range is less than about 25, or 15%, or 10%%, or 5%, or 1%, or 0.1%, or 0.01%, or 0.001, or 0.0001.

Embodiment 50 is the light control film of Embodiment 44, wherein an average optical transmittance of the second region in the predetermined second wavelength range is less than about 25, or 15%, or 10%%, or 5%, or 1%, or 0.1%, or 0.01%, or 0.001, or 0.0001.

Embodiment 51 is the light control film of Embodiment 44, wherein each first region has a substantially high absorption in the predetermined first wavelength range.

Embodiment 52 is the light control film of Embodiment 44, wherein an average optical absorption of each first region in the predetermined second wavelength range is greater than about 70%, or 80%, or 90%, or 95%, or 99%.

Embodiment 53 is the light control film of Embodiment 44, wherein each first region has a substantially high reflectance in the predetermined first wavelength range.

Embodiment 54 is the light control film of Embodiment 44, wherein an average optical reflectance of each first region in the predetermined second wavelength range is greater than about 70%, or 80%, or 90%, or 95%, or 99%.

Embodiment 55 is the light control film of Embodiment 44, wherein each first region has a first index of refraction, and the second region has a second index of refraction, a difference between the first and second indices of refraction being less than about 0.01

Embodiment 56 is the light control film of Embodiment 44, wherein the second region has a substantially low transmission in the predetermined first wavelength range.

Embodiment 57 is the light control film of Embodiment 44, wherein an average optical transmittance of the second region in the predetermined second wavelength range is less than about 10%.

Embodiment 58 is the light control film of Embodiment 44, wherein the second region has a substantially high transmission in the predetermined first wavelength range.

Embodiment 59 is the light control film of Embodiment 44, wherein an average optical transmittance of the second region in the predetermined first wavelength range is greater than about 70%.

Embodiment 60 is the light control film of Embodiment 44, wherein the second region includes a plurality of segments alternating with the plurality of first regions.

Embodiment 61 is the light control film of Embodiment 44, wherein the second region extends across and covers at least some of the first regions.

Embodiment 62 is the light control film of Embodiment 44, wherein the second region is discontinuous.

Embodiment 63 is the light control film of Embodiment 44 including a major microstructured first surface having a plurality of alternating ribs and channels, each channel at least partially filled with a first material to form one of the first regions in the plurality of spaced apart first regions.

Embodiment 64 is the light control film of Embodiment 63, wherein the second region includes a plurality of second region segments, each rib including one of the second region segments.

Embodiment 65 is the light control film of Embodiment 44, wherein the second region is disposed on a major surface of the light control film.

Embodiment 66 is the light control film of Embodiment 44, wherein the second region extends across and covers at least some of the first regions.

Embodiment 67 is a light control film including a plurality of spaced apart first regions and a second region, each first region having a width W and a height H, H/W≥1, each first region having substantially low transmissions in each of non-overlapping predetermined first and second wavelength ranges, the second region having substantially high transmission in the predetermined second wavelength range.

Embodiment 68 is the light control film of Embodiment 67, wherein the predetermined first wavelength range includes shorter wavelengths and the predetermined second wavelength range includes longer wavelengths.

Embodiment 69 is the light control film of Embodiment 67, wherein the predetermined first wavelength range is from about 400 nm to about 700 nm.

Embodiment 70 is the light control film of Embodiment 67, wherein the predetermined second wavelength range is from about 700 nm to about 1200 nm.

Embodiment 71 is the light control film of Embodiment 67, wherein an average optical transmittance of each first region in the predetermined first wavelength range is less than about 10%.

Embodiment 72 is the light control film of Embodiment 67, wherein an average optical transmittance of each first region in the predetermined second wavelength range is less than about 10%.

Embodiment 73 is the light control film of Embodiment 67, wherein an average optical transmittance of the second region in the predetermined second wavelength range is greater than about 70%.

Embodiment 74 is the light control film of Embodiment 67, wherein the second region has a substantially low transmission in the predetermined first wavelength range.

Embodiment 75 is the light control film of Embodiment 67, wherein an average optical transmittance of the second region in the predetermined first wavelength range is less than about 10%.

Embodiment 76 is the light control film of Embodiment 67, wherein the second region has a substantially high transmission in the predetermined first wavelength range.

Embodiment 77 is the light control film of Embodiment 67, wherein an average optical transmittance of the second region in the predetermined first wavelength range is greater than about 70%.

Embodiment 78 is the light control film of Embodiment 67 including a major microstructured first surface having a plurality of alternating ribs and channels, each channel at least partially filled with a first material to form one of the first regions in the plurality of spaced apart first regions.

Embodiment 79 is the light control film of Embodiment 78, wherein the second region includes a plurality of second region segments, each rib including one of the second region segments.

Embodiment 80 is the light control film of Embodiment 67, wherein the second region is disposed on a major surface of the light control film.

Embodiment 81 is the light control film of Embodiment 67, wherein the second region extends across and covers at least some of the first regions.

Embodiment 82 is a light control film including a plurality of spaced apart first regions and a second region, each first region having a width W and a height H, H/W≥1, each first region having a substantially high transmission in a predetermined first wavelength range and a substantially low transmission in a predetermined non-overlapping second wavelength range, the second region having substantially high transmission in each of the predetermined first and second wavelength ranges.

Embodiment 83 is the light control film of Embodiment 82 including a major microstructured first surface having a plurality of alternating ribs and channels, each channel at least partially filled with a first material to form one of the first regions in the plurality of spaced apart first regions.

Embodiment 84 is the light control film of Embodiment 83, wherein the second region includes a plurality of second region segments, each rib including one of the second region segments.

Embodiment 85 is the light control film of Embodiment 82, wherein the second region is disposed on a major surface of the light control film.

Embodiment 86 is the light control film of Embodiment 82, wherein the second region extends across and covers at least some of the first regions.

Embodiment 87 is the light control film of Embodiment 82, wherein the first wavelength range is about 400 nm to about 700 nm.

Embodiment 88 is the light control film of Embodiment 82, wherein the first wavelength range is about 400 nm to about 460 nm.

Embodiment 89 is the light control film of Embodiment 82, wherein the first wavelength range is about 600 nm to about 650 nm.

Embodiment 90 is the light control film of Embodiment 82, wherein the first wavelength range is about 470 nm to about 550 nm.

Embodiment 91 is the light control film of Embodiment 82, wherein a wavelength separation distance between the non-overlapping first and second wavelength ranges is at least 5 nm, or at least 10 nm, or at least 15 nm, or at least 20 nm.

Embodiment 92 is an optical construction including the light control film of Embodiment 82 disposed on a window substrate, each first region having an average optical transmittance of greater than about 50%, or 60%, or 70%, or 80%, or 90% in a first wavelength range from about 400 nm to about 700 nm and an average optical transmittance of less than about 10% in a non-overlapping second wavelength range from about 700 nm to about 1200 nm, the second region having an average optical transmittance of greater than about 30%, or 40%, or 50%, or 60%, or 70%, or 80%, or 90% in each of the predetermined first and second wavelength ranges, wherein the light control film has a viewing angle of less than about 40 degrees for at least one wavelength in the second wavelength range.

Embodiment 93 is the optical construction of Embodiment 92, wherein the window substrate has an average optical transmittance of greater than about 50%, or 60%, or 70%, or 80%, or 90% in the predetermined first and second wavelength ranges.

Embodiment 94 is a light control film including a plurality of spaced apart first regions and a second region, each first region having a width W and a height H, $H/W \geq 1$, each first region having a substantially low transmission in a predetermined first wavelength range and a substantially high transmission in a predetermined non-overlapping second wavelength range, each second region having substantially low transmission in each of the predetermined first and second wavelength ranges.

Embodiment 95 is the light control film of Embodiment 94 including a major microstructured first surface having a plurality of alternating ribs and channels, each channel at least partially filled with a first material to form one of the first regions in the plurality of spaced apart first regions.

Embodiment 96 is the light control film of Embodiment 95, wherein the second region includes a plurality of second region segments, each rib including one of the second region segments.

Embodiment 97 is the light control film of Embodiment 94, wherein the second region is disposed on a major surface of the light control film.

Embodiment 98 is the light control film of Embodiment 94, wherein the second region extends across and covers at least some of the first regions.

Embodiment 99 is a light control film including a plurality of spaced apart first regions and a second region, each first region having a width W and a height H, $H/W \geq 1$, each first region having a substantially high transmission in a predetermined first wavelength range and a substantially low transmission in a predetermined non-overlapping second wavelength range, the second region having substantially low transmission in each of the predetermined first and second wavelength ranges.

Embodiment 100 is the light control film of Embodiment 99 including a major microstructured first surface having a plurality of alternating ribs and channels, each channel at least partially filled with a first material to form one of the first regions in the plurality of spaced apart first regions.

Embodiment 101 is the light control film of Embodiment 100, wherein the second region includes a plurality of second region segments, each rib including one of the second region segments.

Embodiment 102 is the light control film of Embodiment 99, wherein the second region is disposed on a major surface of the light control film.

Embodiment 103 is the light control film of Embodiment 99, wherein the second region extends across and covers at least some of the first regions.

Embodiment 104 is a light control film including a plurality of spaced apart first regions and a second region, each first region having a width W and a height H, $H/W \geq 1$, each first region having a substantially low transmission in a predetermined first wavelength range and a substantially high transmission in a predetermined non-overlapping second wavelength range, the second region having substantially high transmission in each of the predetermined first and second wavelength ranges.

Embodiment 105 is the light control film of Embodiment 104 including a major microstructured first surface having a plurality of alternating ribs and channels, each channel at least partially filled with a first material to form one of the first regions in the plurality of spaced apart first regions.

Embodiment 106 is the light control film of Embodiment 105, wherein the second region includes a plurality of second region segments, each rib including one of the second region segments.

Embodiment 107 is the light control film of Embodiment 104, wherein the second region is disposed on a major surface of the light control film.

Embodiment 108 is the light control film of Embodiment 104, wherein the second region extends across and covers at least some of the first regions.

Embodiment 109 is a light control film configured to block light in a predetermined wavelength range, including a plurality of spaced apart first regions, each first region having a width W and a height H, $H/W \geq 1$, each first region having a substantially high transmission in a predetermined first wavelength range, a substantially low transmission in a predetermined second wavelength range, and a substantially high transmission in a predetermined third wavelength range, the second wavelength range disposed between the first and third wavelength ranges Embodiment 110 is the light control film of Embodiment 109, wherein the second wavelength range is about 20 nm wide from a first wavelength to a second wavelength and centered on a laser visible emission wavelength, the first wavelength range is from about 400 nm to about the first wavelength, and the third wavelength range is from about the second wavelength to about 1400 nm.

Embodiment 111 is the light control film of Embodiment 110, wherein the laser visible emission wavelength is at least one of 442 nm, 458 nm, 488 nm, 514 nm, 632.8 nm, 980 nm, 1047 nm, 1064 nm, and 1152 nm.

Embodiment 112 is the light control film of Embodiment 110, wherein the laser visible emission wavelength is in a range from about 416 nm to about 1360.

Embodiment 113 is the light control film of Embodiment 109 further including a plurality of spaced apart second regions alternating with the plurality of first regions, each second region having a substantially high transmission in each of the predetermined first, second and third wavelength ranges.

Embodiment 114 is the light control film of Embodiment 109 having a viewing angle of less than about 60 degrees, or 50 degrees, or 40 degrees, or 30 degrees, or 20 degrees in the predetermined second wavelength range.

Embodiment 115 is a light control film including a plurality of spaced apart first regions and a second region, such that for light incident normally to a plane of the light control film:
an average optical transmittance of the light control film is less than about 10% in a predetermined first wavelength range having shorter wavelengths; and
an average optical transmittance of the light control film is greater than about 50% in a predetermined second wavelength range having longer wavelengths; and for light incident at or greater than about 30 degrees from the plane of the light control film:
an average optical transmittance of the light control film is less than about 20% in each of the predetermined first and second wavelength ranges.

Embodiment 116 is the light control film of Embodiment 115, wherein the predetermined first wavelength range is from about 400 nm to about 650 nm, and the predetermined second wavelength range is from about 750 nm to about 1500 nm.

Embodiment 117 is the light control film of Embodiment 115, wherein the second region includes a plurality of spaced apart second region segments alternating with the plurality of first regions.

Embodiment 118 is the light control film of Embodiment 115 including a major micro structured first surface having a plurality of alternating ribs and channels, each channel at least partially filled with a first material to form one of the first regions in the plurality of spaced apart first regions.

Embodiment 119 is the light control film of Embodiment 118, wherein the second region includes a plurality of second region segments, each rib including one of the second region segments.

Embodiment 120 is the light control film of Embodiment 115, wherein the second region is disposed on a major surface of the light control film.

Embodiment 121 is the light control film of Embodiment 115, wherein the second region extends across and covers at least some of the first regions.

Embodiment 122 is the light control film of Embodiment 115, wherein an average optical transmittance of the first regions in the predetermined second wavelength range is less than about 20%, or less than about 15%, or less than about 10%, or less than about 5%, or less than about 1%.

Embodiment 123 is the light control film of Embodiment 115, wherein an average optical transmittance of the second region in the predetermined first wavelength range is less than about 20%, or less than about 15%, or less than about 10%, or less than about 5%, or less than about 1%.

Embodiment 124 is the light control film of Embodiment 115, wherein an average optical transmittance of the second region in the predetermined second wavelength range is greater than about 40%, or greater than about 50%, or greater than about 60%, or greater than about 70%, or greater than about 80%, or greater than about 90%.

Embodiment 125 is the light control film of Embodiment 115, wherein for light incident normally to the plane of the light control film, the average optical transmittance of the light control film is less than about 5% in the predetermined first wavelength range.

Embodiment 126 is the light control film of Embodiment 115, wherein for light incident normally to the plane of the light control film, the average optical transmittance of the light control film is less than about 1% in the predetermined first wavelength range.

Embodiment 127 is the light control film of Embodiment 115, wherein for light incident normally to the plane of the light control film, the average optical transmittance of the light control film is greater than about 55% in the predetermined second wavelength range.

Embodiment 128 is the light control film of Embodiment 115, wherein for light incident normally to the plane of the light control film, the average optical transmittance of the light control film is greater than about 60% in the predetermined second wavelength range.

Embodiment 129 is a light control film including a plurality of spaced apart first regions and a second region, such that when an angle of incidence of light incident on the light control film changes from about 90 degrees to about 60 degrees relative to a plane of the light control film, an average optical transmittance of the light control film changes by:
less than about 10% in a predetermined first wavelength range having shorter wavelengths; and
greater than about 40% in a predetermined second wavelength range having longer wavelengths.

Embodiment 130 is the light control film of Embodiment 129, wherein the predetermined first wavelength range is from about 400 nm to about 650 nm, and the predetermined second wavelength range is from about 750 nm to about 1500 nm.

Embodiment 131 is the light control film of Embodiment 129, wherein the second region includes a plurality of spaced apart second region segments alternating with the plurality of first regions.

Embodiment 132 is the light control film of Embodiment 129 including a major microstructured first surface having a plurality of alternating ribs and channels, each channel at least partially filled with a first material to form one of the first regions in the plurality of spaced apart first regions.

Embodiment 133 is the light control film of Embodiment 132, wherein the second region includes a plurality of second region segments, each rib including one of the second region segments.

Embodiment 134 is the light control film of Embodiment 129, wherein the second region is disposed on a major surface of the light control film.

Embodiment 135 is the light control film of Embodiment 129, wherein the second region extends across and covers at least some of the first regions.

Embodiment 136 is the light control film of Embodiment 129, wherein an average optical transmittance of the first regions in the predetermined second wavelength range is less than about 20%, or less than about 15%, or less than about 10%, or less than about 5%, or less than about 1%.

Embodiment 137 is the light control film of Embodiment 129, wherein an average optical transmittance of the second region in the predetermined first wavelength range is less than about 20%, or less than about 15%, or less than about 10%, or less than about 5%, or less than about 1%.

Embodiment 138 is the light control film of Embodiment 129, wherein an average optical transmittance of the second region in the predetermined second wavelength range is greater than about 40%, or greater than about 50%, or greater than about 60%, or greater than about 70%, or greater than about 80%, or greater than about 90%.

Embodiment 139 is the light control film of Embodiment 129, wherein when the angle of incidence of light incident on the light control film changes from about 90 degrees to about 60 degrees relative to the plane of the light control film, the average optical transmittance of the light control film changes by less than about 5% in the predetermined first wavelength range.

Embodiment 140 is the light control film of Embodiment 129, wherein when the angle of incidence of light incident on the light control film changes from about 90 degrees to about 60 degrees relative to the plane of the light control film, the average optical transmittance of the light control film changes by less than about 1% in the predetermined first wavelength range.

Embodiment 141 is the light control film of Embodiment 129, wherein when the angle of incidence of light incident on the light control film changes from about 90 degrees to about 60 degrees relative to the plane of the light control film, the average optical transmittance of the light control film changes by greater than about 55% in the predetermined second wavelength range.

Embodiment 142 is the light control film of Embodiment 129, wherein when the angle of incidence of light incident on the light control film changes from about 90 degrees to about 60 degrees relative to the plane of the light control film, the average optical transmittance of the light control film changes by greater than about 60% in the predetermined second wavelength range.

Embodiment 143 is a light control film including:
a major microstructured first surface having a plurality of alternating ribs and channels, each channel at least partially filled with a first material to form a first region; and
a second region adjacent at least a portion of at least one first region and including a second material;
wherein each of the first and second materials absorbs light in one or two of a first wavelength range from about 300 nm to about 400 nm, a second wavelength range from about 400 nm to about 700 nm, and a third wavelength range from about 700 nm to about 1200 nm, and wherein each channel includes a width W and a height H, H/W≥1.

Embodiment 144 is the light control film of Embodiment 143, wherein the second region is disposed in or on at least portions of the ribs.

Embodiment 145 is the light control film of Embodiment 143, wherein the second region includes a plurality of second region segments, each rib including one of the second region segments.

Embodiment 146 is the light control film of Embodiment 143, wherein the second region is disposed on a major surface of the light control film.

Embodiment 147 is the light control film of Embodiment 143, wherein the second region extends across and covers at least some of the first regions.

Embodiment 148 is a light source system, including:
a light source configured to emit light having a first spectral profile along a first direction and a second spectral profile along a different second direction; and
a light control film disposed on the light source for receiving and transmitting light emitted by the light source, the light control film including a plurality of spaced apart first regions, each first region having a width W and a height H, H/W≥1, the first regions oriented relative to the first and second directions and having a spectral absorbance profile so that when light emitted by the light source is transmitted by the light control film, the transmitted light has a third spectral profile along the first direction and a fourth spectral profile along the second direction, a difference between the third and fourth spectral profiles being less than a difference between the first and second spectral profiles.

Embodiment 149 is the light source system of Embodiment 148, wherein the first direction is substantially perpendicular to a plane of the light control film.

Embodiment 150 is the light source system of Embodiment 148, wherein each first region selectively absorbs light within each of the first and second spectral profiles.

Embodiment 151 is the light source system of Embodiment 148, wherein light emitted from the light source propagating along the first direction has a first set of color coordinates and propagating along the second direction has a second set of color coordinates, wherein light transmitted by the light control film propagating along the first direction has a third set of color coordinates and propagating along the second direction has a fourth set of color coordinates, a difference between the third and fourth sets of color coordinates being less than a difference between the first and second sets of color coordinates.

Embodiment 152 is a retroreflective system, including:
a retroreflective sheet for retroreflecting light; and
a light control film disposed on the retroreflective sheet, such that for a first wavelength, light incident on the light control film at each of a first and second angles of incidence is retroreflected, and for a second wavelength, light incident on the light control film at the first, but not the second, angle of incidence is retroreflected.

Embodiment 153 is the retroreflective system of Embodiment 152, wherein the light control film includes a greater first viewing angle for the first wavelength and a smaller viewing angle for the second wavelength.

Embodiment 154 is the retroreflective system of Embodiment 152, wherein the first angle of incidence is substantially equal to zero relative to a line normal to a plane of the light control film.

Embodiment 155 is the retroreflective system of Embodiment 152, wherein the retroreflective sheet includes at least one of microsphere beads and corner cubes.

Embodiment 156 is the retroreflective system of Embodiment 152, wherein the light control film includes a plurality of spaced apart first regions, each first region having a substantially low transmission at the second, but not the first, wavelength.

Embodiment 157 is the detector system of Embodiment 38, wherein the detector includes a photovoltaic device.

Embodiment 158 is the detector system of Embodiment 38, wherein the detector includes a solar battery, a solar cell, or a solar detector.

Embodiment 159 is the detector system of Embodiment 38, wherein the detector is a detector in a camera.

Embodiment 160 is a camera including the detector system of Embodiment 38.

Embodiment 161 is the light source system of Embodiment 148, wherein the light source includes a light emitting diode (LED), a laser light source, a halogen light source, a metal halide light source, a tungsten light source, a mercury vapor light source, a short arc xenon light source, or the sun.

Unless otherwise indicated, all numbers expressing feature sizes, amounts, and physical properties used in the specification and claims are to be understood as being modified by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A detector system, comprising:
    a detector sensitive to wavelengths in a detection wavelength range; and
    a light control film disposed on the detector and comprising a plurality of alternating first and second regions, each first region having a width W and a height H, H/W≥1, each first region having a substantially low transmission in a first portion of the detection wavelength range and a substantially high transmission in a remaining portion of the detection wavelength range, each second region having a substantially high transmission in the detection wavelength range.

2. The detector system of claim 1, wherein the detection wavelength range is from about 800 nm to about 1600 nm and the first portion of the detection wavelength range is from about 900 nm to about 1100 nm.

3. The detector system of claim 1, wherein a viewing angle of the light control film in the first portion of the detection wavelength range is less than about 70 degrees along a first direction.

4. The detector system of claim 1, wherein the light control film comprises a major microstructured first surface having a plurality of alternating ribs and channels, each channel at least partially filled with a first material to form one of the first regions, each rib comprising a second material and forming one of the second regions.

5. The detector system of claim 1, wherein H/W≥5.

6. The detector system of claim 1, wherein H/W≥10.

7. The detector system of claim 1, wherein the detector comprises a photovoltaic device.

8. The detector system of claim 1, wherein the detector comprises a solar battery, a solar cell, or a solar detector.

9. The detector system of claim 1, wherein the detector is a detector in a camera.

10. A camera comprising the detector system of claim 1.

* * * * *